(12) United States Patent
Kahatt et al.

(10) Patent No.: US 12,060,548 B2
(45) Date of Patent: Aug. 13, 2024

(54) FLUID HANDLING APPARATUS

(71) Applicant: Spartan Bioscience Inc., Ottawa (CA)

(72) Inventors: Espir Kahatt, Carlsbad, CA (US);
Chris Harder, Dunrobin (CA);
Louwrens Stassen, Kanata (CA);
Marie Ashman, Ottawa (CA); Peter Goodings, Ottawa (CA); Saakshi Sutarwala, Ottawa (CA)

(73) Assignee: Genomadix Inc., Ottawa (CA)

( * ) Notice: Subject to any disclaimer, the term of this patent is extended or adjusted under 35 U.S.C. 154(b) by 1030 days.

(21) Appl. No.: 16/962,331

(22) PCT Filed: Jan. 18, 2019

(86) PCT No.: PCT/CA2019/050070
§ 371 (c)(1),
(2) Date: Jul. 15, 2020

(87) PCT Pub. No.: WO2019/140532
PCT Pub. Date: Jul. 25, 2019

(65) Prior Publication Data
US 2020/0339928 A1 Oct. 29, 2020

Related U.S. Application Data

(60) Provisional application No. 62/619,661, filed on Jan. 19, 2018.

(51) Int. Cl.
*C12M 1/00* (2006.01)
*C12M 1/12* (2006.01)
*G01N 1/40* (2006.01)

(52) U.S. Cl.
CPC ............ *C12M 23/38* (2013.01); *C12M 23/40* (2013.01); *C12M 37/02* (2013.01); *C12M 37/04* (2013.01);
(Continued)

(58) Field of Classification Search
CPC ...... C12M 23/38; C12M 23/40; C12M 37/02; C12M 37/04; G01N 1/4077; G01N 2001/4088
See application file for complete search history.

(56) References Cited

U.S. PATENT DOCUMENTS 9,435,440 B2   9/2016  Gamache
2007/0144594 A1*  6/2007  Moon ................. F16K 37/0058
                                              137/625.46
(Continued)

FOREIGN PATENT DOCUMENTS

CA   2668639 A1   5/2008
CA   2764464 A1   12/2010
(Continued)

OTHER PUBLICATIONS

Desheng ("A degassing plate with hydrophobic bubble capture and distributed venting for microfluidic devices").Dennis Desheng Meng et al 2006 J. Micromech. Microeng. 16 419 DOI 10.1088/0960-1317/16/2/028 DownloadArticle PDF (Year: 2006).*
(Continued)

*Primary Examiner* — Jennifer Wecker
*Assistant Examiner* — Jonathan Bortoli
(74) *Attorney, Agent, or Firm* — Choate, Hall & Stewart LLP; Charles E. Lyon

(57) ABSTRACT

A fluid handling apparatus having a two-sided channel plate with channel ports extending from one side to the other. Fluid channels on both sides of the channel plate connected to the channel ports direct fluid through the channel plate in a desired fluid path, and the first face and the second face of the channel plate are sealed to fluidly encase the fluid channels.

34 Claims, 25 Drawing Sheets

(52) U.S. Cl.
CPC ... *G01N 1/4077* (2013.01); *G01N 2001/4088* (2013.01)

(56) References Cited

U.S. PATENT DOCUMENTS

| | | | | |
|---|---|---|---|---|
| 2011/0005932 | A1* | 1/2011 | Jovanovich | C12Q 1/6806 |
| | | | | 204/453 |
| 2011/0256630 | A1* | 10/2011 | Clinton | G01N 35/00871 |
| | | | | 422/68.1 |
| 2012/0115705 | A1* | 5/2012 | Sharon | B04B 5/0407 |
| | | | | 494/56 |
| 2012/0244043 | A1* | 9/2012 | Leblanc | B01L 3/502715 |
| | | | | 422/504 |
| 2012/0308445 | A1* | 12/2012 | Roper | G01N 1/312 |
| | | | | 210/322 |
| 2015/0136602 | A1* | 5/2015 | Jovanovich | G01N 27/44721 |
| | | | | 204/601 |
| 2015/0184224 | A1 | 7/2015 | Guy et al. | |
| 2017/0002395 | A1* | 1/2017 | Baumstummler | C12Q 1/22 |

FOREIGN PATENT DOCUMENTS

| | | | | |
|---|---|---|---|---|
| DE | 102013215065 | A1 * | 2/2015 | G01N 30/20 |
| WO | WO-2015/187849 | A2 | 12/2015 | |

OTHER PUBLICATIONS

English translation of DE-102013215065-A1 (Year: 2015).*
International Search Report for PCT/CA19/050070, 5 pages (mailed Apr. 3, 2020).
Written Opinion for PCT/CA19/050070, 6 pages (mailed Apr. 3, 2020).

* cited by examiner

Fig. 12A                    Fig. 12B

FLUID HANDLING APPARATUS

This application is a U.S. National Phase Application under 35 U.S.C. § 371 of International Patent Application No. PCT/CA2019/050070, filed on Jan. 18, 2019, which claims the benefit of and priority to U.S. Provisional Application No. 62/619,661, filed on Jan. 19, 2018, the entire contents of each of which are hereby incorporated by reference in their entireties.

FIELD OF THE INVENTION

The present invention relates in general to a fluid handling apparatus. More particularly, the present invention pertains to a fluid handling apparatus having a channel plate having fluid channels on both sides of the channel plate.

BACKGROUND

Detection and control of microbiological organisms are important in health care, environmental regulation, biowarfare, forensics, pathogen identification, food and drug testing, and in a variety of industrial systems. In industry, the presence of undesirable microorganisms can lead to contamination of products and the environment, and can decrease the efficiency of operating equipment. Furthermore, since microorganisms multiply rapidly, the presence of pathogenic microorganisms also causes health risks to the public. There is an increasing concern with pathogenic organisms infecting water and process systems and creating human, animal, and environmental health risk.

The difficulties of detecting and quantifying dilute biological materials in liquids are well known. As the concentration of microorganisms decreases in a sample, so does the ease and ability to detect the microorganism. This can pose a significant risk where even small amounts of a pathogenic organism can lead to contamination or human infection. In cooling towers, for example, water borne pathogenic microorganisms such as *Legionella* sp. may be present. If not properly treated, aerosolized particles containing the microorganisms can cause human disease such as Legionnaires' disease caused by *Legionella pneumophila*. Detection of this microorganism in particular is difficult in the case of open recirculation water systems such as cooling towers because even low concentrations of bacteria represent serious health risk, however detecting such low concentrations can be time consuming and resource intensive. Also, large water volumes must be concentrated into smaller sample volumes in order to perform the desired analytical test to obtain accurate and reproducible results.

Concentration of biological particles suspended in liquid from a dilute source is advantageous for detection of microbiological particles because it is easier to detect and quantify concentrated samples in a small volume. Various methods exist for concentrating microorganisms in liquids prior to detection. In one example, particle concentration in liquid can be performed using centrifugation, which separates mixtures according to differences in the density of the individual components present in the mixture, forming a pellet of relatively dense material at the bottom of a centrifuge tube. Another common method is to enrich the sample in nutrient broth and then cultivate an aliquot of the broth on an agar plate. A disadvantage of this method is the time requirement, as it normally takes five to seven days before organisms can be quantified on the plates. Other concentration methods include various filtration based methods, adsorption-elution, immunocapture and flocculation. These methods for concentrating a large volume of water into a very small sample volume generally require large and complex laboratory equipment and as well as time and technical expertise.

To accurately quantify small amounts of microorganisms in a sample, for example by quantitative polymerase chain reaction (qPCR), one must concentrate a known amount of sample, and then analyze a known amount of the concentrated sample. In a laboratory, this concentration could be performed by passing a known amount of sample through a filter, eluting a known amount of the concentrated sample, and then performing qPCR on a known aliquot of the concentrated sample. Typically, this requires specialized training or specialized equipment to accurately collect and dispense known quantities of samples e.g., with a pipette. Field sampling, preparation and analysis of samples for microbiological contamination can be complicated and costly and require a trained technician. There remains a need for a sample concentrating apparatus and method which can be done easily with rapid and reliable results and by a person with limited training.

Rotary flow path switching valves have been used in high performance liquid chromatography, hematology, and in process chemistry, for transferring liquid sample along a fluid path. In an example, U.S. Pat. No. 9,435,440 to Gamache describes a method for channeling a fluid through different passages of a valve comprising the use of a valve element which can move between different positions so as to permit or obstruct communication between the fluid passages, and a biasing element to bias the valve element against a body interface.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a fluid handling apparatus having a two-sided channel plate with channel ports extending from one side to the other. Fluid channels on both sides of the channel plate connected to the channel ports direct fluid through the channel plate in a desired fluid path.

In an aspect there is provided a fluid handling apparatus comprising: a channel plate having a first face and a second face, the channel plate comprising: a plurality of channel ports extending from the first face to the second face for directing fluid between the first face and the second face of the channel plate; a plurality of fluid channels, the fluid channels on the first face and the second face of the channel plate, each fluid channel fluidly connected to at least one channel port; a sample port for receiving fluid to be handled, the sample port fluidly connected to at least one of the plurality of fluid channels; and an exit port for extracting fluid from the fluid handling apparatus, wherein the first face and the second face of the channel plate are sealed to fluidly encase the fluid channels.

In an embodiment of the apparatus, the first face and the second face of the channel plate are sealed with a sealing film.

In another embodiment of the apparatus, the channel plate has a top side and a bottom side, and wherein the channel plate comprises fluid channels on both the top side and the bottom side.

In another embodiment, the apparatus further comprises a hydrophobic vent in at least one of the plurality of fluid channels.

In another embodiment of the apparatus, the plurality of channel ports are arranged annularly around an axis.

In another embodiment of the apparatus, the channel plate is fluidly connected to a waste reservoir.

In another embodiment of the apparatus, the channel plate further comprises a wash aperture.

In another embodiment, the apparatus further comprises a base.

In another embodiment, the apparatus further comprises a filter fluidly connected to at least one of the plurality of fluid channels.

In another embodiment, the apparatus further comprises a valve plate movable relative to the channel plate, the valve plate comprising at least one channel valve to fluidly connect at least two of the plurality of channel ports and fluid channels.

In another embodiment of the apparatus, the valve plate is compressible against the channel plate.

In another embodiment of the apparatus, the valve plate comprises at least one of elastomer and an elastomer gasket.

In another embodiment, the apparatus further comprises a compression plate to compress the channel valve of the valve plate against the channel plate.

In another embodiment of the apparatus, the valve plate comprises a plurality of channel valves.

In another embodiment of the apparatus, the valve plate is a rotary valve comprising: a top surface comprising a knob to control rotation of the rotary valve about a central axis; and a bottom surface comprising the at least one channel valve.

In another embodiment, the apparatus further comprises an annular housing to support the rotary valve, and the rotary valve and housing comprises complimentary alignment pins and rotation guides to angularly align the rotary valve relative to the plurality of channel ports.

In another embodiment of the apparatus, the compression plate and rotary valve comprise complimentary divets and compression bumps to bias the rotary valve against the channel plate.

In another embodiment, the apparatus further comprises a cover.

In another embodiment of the apparatus, the cover is movable relative to the base.

In another embodiment of the apparatus, the cover is rotatable relative to the base.

In another embodiment of the apparatus, the channel plate is supported by a sidewall.

In another aspect there is provided a method of concentrating a microbiological fluid sample, the method comprising: injecting a dilute microbiological sample into a channel on a channel plate; directing the dilute microbiological sample onto a filter; filtering the dilute microbiological sample; collecting concentrated microbiological fraction off the filter; moving the concentrated microbiological sample taken off the filter into a channel; and ejecting the concentrated microbiological sample into a sample vial.

In an embodiment, the method further comprises analyzing the concentrated microbiological sample.

In another embodiment of the method, analyzing the concentrated fluid comprises polymerase chain reaction.

In an embodiment, the method further comprises calculating the concentration of microbiological material in the concentrated microbiological sample.

In an embodiment, the method further comprises calculating the concentration of microbiological material in the dilute microbiological sample.

In an embodiment, the method further comprises washing the filter.

In another embodiment, the dilute microbiological sample comprises at least one of bacteria, algae, fungi, protozoa, and parasitoids.

In another embodiment, the bacteria is *Legionella pneumophila*.

In another aspect there is provided a sample concentrating kit comprising: a sample concentrating apparatus comprising: a channel plate comprising: a sample port for receiving dilute sample fluid; a plurality of channel ports extending through the channel plate; a plurality of fluid channels connected to the channel ports, the plurality of fluid channels fluidly encased; and a filter fluidly connected to one of the plurality of fluid channels for receiving dilute sample fluid from the sample port; and a valve plate movable relative to the channel plate, the valve plate comprising at least one channel valve to fluidly connect at least two of the plurality of channel ports and fluid channels; and a sample syringe.

In another aspect there is provided a sample concentrating apparatus comprising: a channel plate having a first face and a second face, the channel plate comprising: a plurality of channel ports extending from the first face to the second face for directing fluid between the first face and the second face of the channel plate; a plurality of fluid channels, the fluid channels on the first face and the second face of the channel plate, each fluid channel fluidly connected to at least one channel port; a sample port for receiving dilute fluid sample to be handled, the sample port fluidly connected to at least one of the plurality of fluid channels; a filter for receiving dilute fluid sample from the sample port; and an exit port for extracting fluid from the fluid handling apparatus, wherein the first face and the second face of the channel plate are sealed to fluidly encase the fluid channels.

In an embodiment, the first face and the second face of the channel plate are sealed with a sealing film.

In another embodiment, the apparatus further comprises a hydrophobic vent in at least one of the plurality of fluid channels.

In another embodiment, the plurality of channel ports are arranged annularly around an axis.

In another embodiment, the apparatus further comprises a rotary valve comprising: a top surface comprising a knob to control rotation of the rotary valve about the axis; and a bottom surface comprising at least one channel valve.

In another embodiment, the channel plate is fluidly connected to a waste reservoir.

In another embodiment, the channel plate further comprises a wash aperture.

In another embodiment, the apparatus further comprises a base.

In another aspect there is provided channel plate for fluid handling, the channel plate comprising: a first face; a second face; a plurality of channel ports extending from the first face to the second face for directing fluid between the first face and the second face; a plurality of fluid channels, the fluid channels on the first face and the second face, each fluid channel fluidly connected to at least one channel port; a sample port for receiving fluid to be handled, the sample port fluidly connected to at least one of the plurality of fluid channels; and an exit port for extracting fluid from the fluid handling apparatus, wherein the first face and the second face are sealed to fluidly encase the fluid channels.

In another embodiment, the channel plate further comprises a filter.

In another embodiment, the channel plate further comprises a hydrophobic vent.

BRIEF DESCRIPTION OF THE FIGURES

For a better understanding of the present invention, as well as other aspects and further features thereof, reference is made to the following description which is to be used in conjunction with the accompanying drawings, where:

FIG. 12A is a perspective view of the inside of the compression ring;

FIG. 12B is a perspective view of the top of the compression ring;

DETAILED DESCRIPTION OF THE INVENTION

Figure 1A:
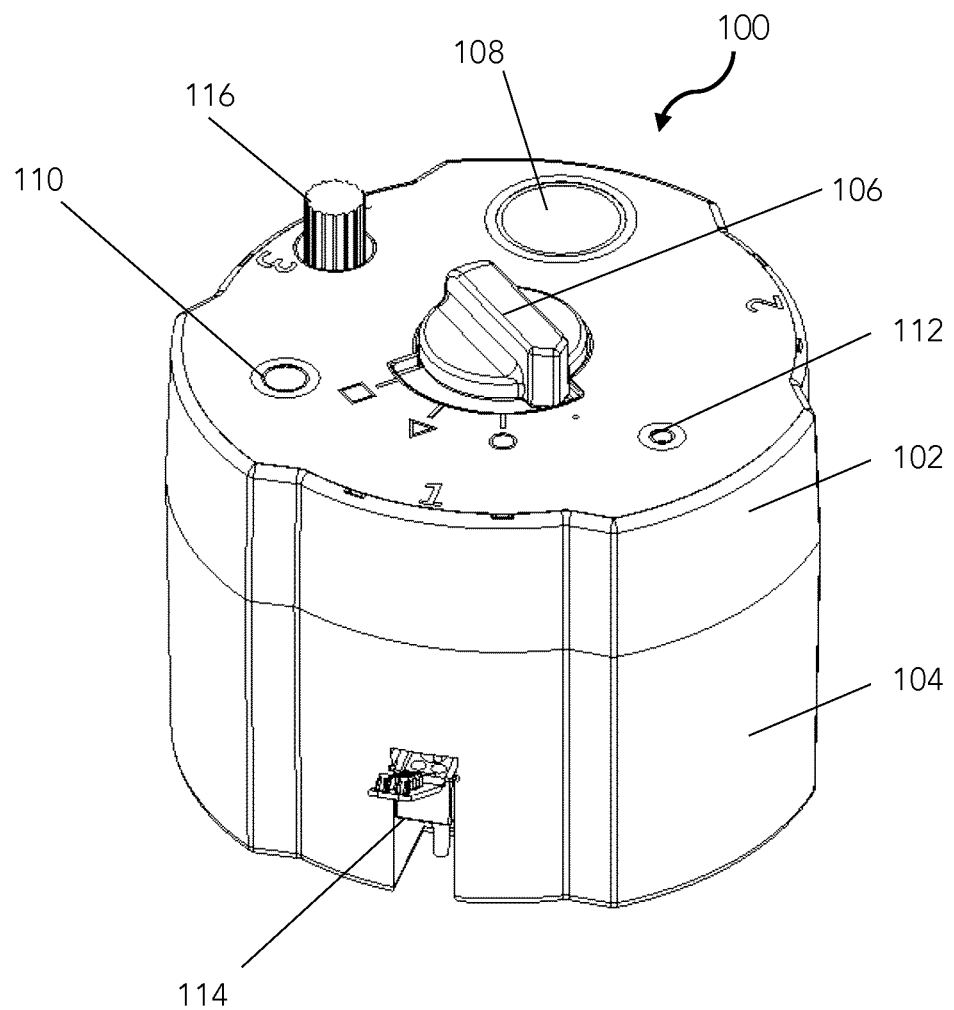
FIG. 1A is a perspective view of a rotary sample concentrating apparatus.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

Herein is described an apparatus, method and kit for fluid directing and fluid handling on a two-sided channel plate. The channel plate can be used, in particular, for fluid direction, as well as pressure-assisted concentrating of microbiological particles from a dilute fluid sample. In particular, the channel plate comprises a plurality of channel ports extending through the channel plate to direct fluid from one side of the channel plate to the other, and a plurality of fluid channels on each side of the channel plate to direct the fluid to different locations according to the fluid handling need. An additional valve plate movable relative to channel plate can be used to direct fluid flow in the channel plate by connecting the channel ports and fluid channels.

The present apparatus can be used to concentrate microbiological particles and microorganisms that are suspended in a liquid sample from a dilute feed suspension. Dilute sample fluid entering the apparatus can be filtered with a filter fluidly connected to one or the channel ports or fluid channels to collect any microbiological material, and concentrated sample fluid can be directed through the channel plate into a sample vial. Fluid sample can be concentrated from a variety of fluids, aqueous samples, or suspended solids from a variety of sources. Non-limiting sources of sample to be concentrated can include aqueous samples from agricultural products and livestock environments, forensic samples, environmental samples, wash fluid, bodily fluid, and samples from building systems such as reservoirs, water tanks and heating, ventilation, and air conditioning (HVAC) water systems. Food substances such as beverages including fruit juices, vegetable juices, carbonated beverages, alcoholic beverages and homogenates or liquid samples produced from solid foods can also be sampled.

Manual swabbing of surfaces onto wetted swabs, pads, or pieces of filter material taken for bioterrorism, industrial, medical, environmental, health, and security monitoring can also be suspended in fluid and concentrated. Microbiological particles trapped by the filter can be cellular microbiological organisms selected from the group consisting of bacteria, algae, fungi, protozoa, parasitoids, and combinations thereof. Biologics to be concentrated can include bacteria such as but not limited to *Bacillus anthracis, Yersinia pestis, Escherichia coli, Vibrio cholerae, Burkholderia mallei*, and other bacteria from the genus *francisella, brucella, clostridium, salmonella, shigella, legionella, chlamydia, coxiella, staphylococcus, rickettsia, mycobacterium, bartonella*, and *neisseria*. Parasitic protozoans such as from the genus *cryptosporidium* and fungi including pathogenic fungi can also be concentrated. Examples of fungi that can be concentrated and collected include but are not limited to *Histoplasma capsulatum, Aspergillus niger, Apophysomyces elegans, Candida, blastoschizomyces, cladophialophora* and *saccharomyces*, amongst others.

The present apparatus may be entirely manually operated using manually applied pressures while still providing adequate pressure to direct fluid through the flow path on the channel plate. Further, the present method for concentrating dilute samples comprising microbiological material can be done at the site of collection in the field and does not require specialized lab equipment. Analysis can also be done in the field with a mobile PCR analyzer, such as for example the Spartan Cube.

By knowing the volume of dilute fluid sample injected onto the apparatus with subsequent quantitative testing of the concentrated sample, a measurement of the concentration of microbiological material in the dilute fluid sample can also be made. The known volume of dilute fluid sample which provides a known volume of concentrate for analysis can be used to extrapolate the concentration of microbiological material in the fluid sample. Subsequent analysis on the concentrated sample can identify and also quantify the microbiological material present in the dilute sample.

A fluid handling apparatus 100 is shown in FIG. 1A. The shown sample apparatus comprises a cover 102 and base 104, with midlayer (not shown) nestled inside and between the cover 102 and base 104. Knob 106 is coupled inside the apparatus to a rotary valve which acts as a valve plate and rotates with knob 106. Knob 106 shown is manual and has a plurality of angular settings as shown by the dot (•), circle (○), triangle (Δ), and square (☒) on the top surface of the cover 102. The cover 102 comprises a sample aperture 108 sized to receive a sample syringe comprising dilute sample to be tested, which is connected to a filter for trapping microbiological particles by rotation of the rotary valve. The amount of dilute sample injected onto the filter can be, for example 1 mL-100 mL, though can also be more or less. The sample aperture can also be configured to be fluidly connected to other fluidic devices such as any tube or chamber that can be pressurized to inject fluid onto the channel plate.

Wash aperture 110 shown is sized to receive a syringe comprising a wash liquid, for example a syringe of 5 mL-100 mL volume size. A wash fluid can be applied to the filter through wash aperture 110 from a wash syringe after dilute sample fluid has been passed through the filter and microbiological material of interest is retained on the filter. A cleaning/washing cycle of the filter can thereby be undertaken inside the apparatus without having to dismantle or disassemble the apparatus by applying a cleaning fluid to the filter from the wash aperture 110. An additional fluid can be applied through the sample aperture 108 or wash aperture 110, such as, for example wash fluid or other fluid. Washing the filter with liquid removes dissolved material and small particles, including inhibitors that may interfere with later analysis of the concentrated sample, while the microbiological material of interest is retained on the filter. Micro port 112 is sized to receive a micro syringe barrel. The front of the base 104 has a sample vial port 114 for supporting and receiving a sample vial where concentrated sample is ejected. Capping rod cap 116 protects the capping rod (internal, not shown) and is removed when the sample vial is ready to be capped.

Figure 1B:
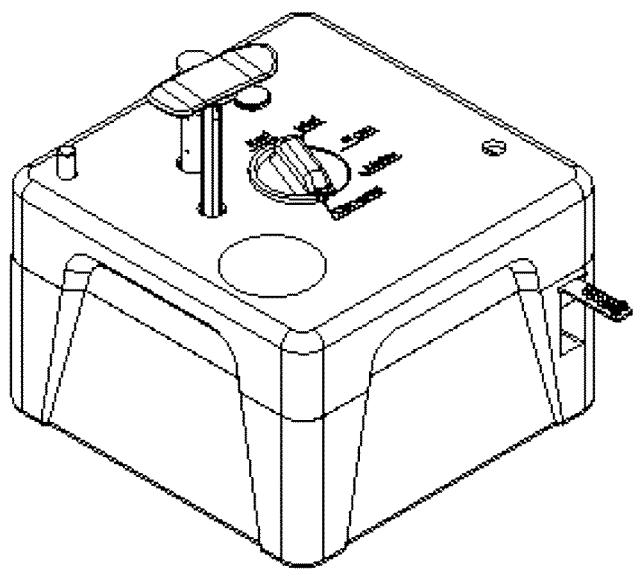
FIGS. 1B and 1C are perspective views of two rotary valve concentrating apparatuses with alternative housing configurations.
Figure 1C:
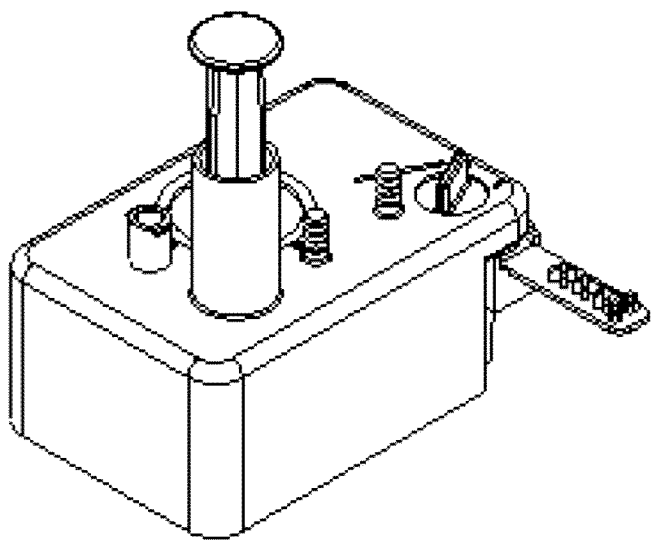

FIGS. 1B and 1C show two alternative housing configurations of a fluid handling apparatus, with square and rectangular housing shapes, respectively. It is understood that the channel plate can also have variable size and shape to accommodate the fluid handling requirements of the apparatus.

Figure 2A:
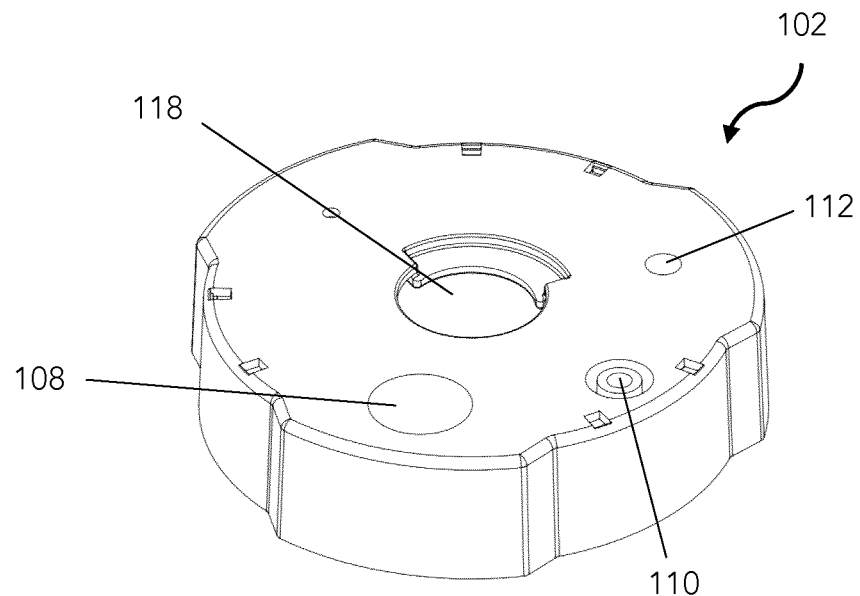
FIG. 2A is a top perspective view of the cover of the concentrating apparatus.

FIG. 2A is a top perspective view of the cover 102 of a fluid handling apparatus comprising a sample aperture 108, wash aperture 110, and micro aperture 112. In the cover, sample aperture 108, wash aperture 110, and micro aperture 112 are apertures aligned with fluid channels in the channel plate to direct transfer and/or manipulate fluid in the channel plate. Cover 102 mates with the channel plate and the base to form an integrated concentrating apparatus. The cover has a knob aperture 118 for receiving and seating the knob to control the rotary valve in a way that the knob and rotary valve can rotate to a plurality of angular positions relative to the cover 102. Secure attachment of the cover 102 to the channel plate enables rotation of the combined cover and channel plate relative to the base.

Figure 2B:
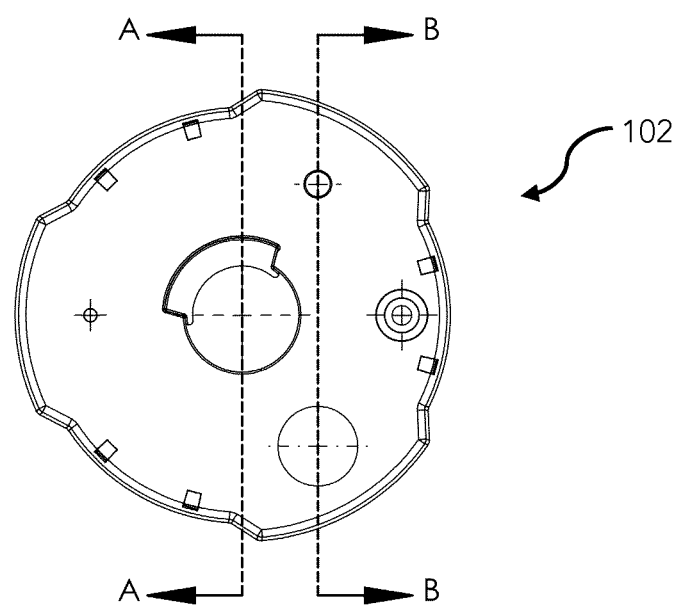
FIG. 2B is a top view of the top of the cover of the concentrating apparatus.
Figure 2C:
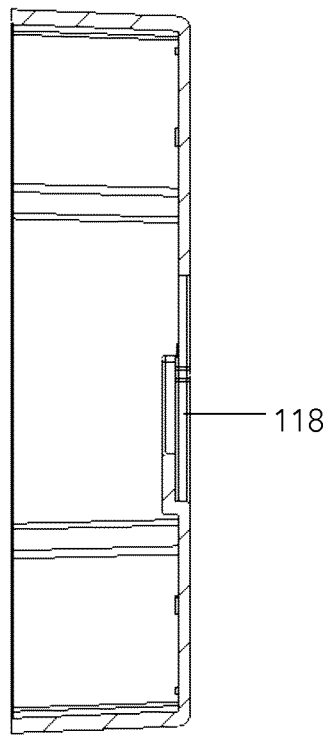
FIG. 2C is a side cross-sectional view of the cover of the concentrating apparatus along line A-A as shown in FIG. 2B.
Figure 2D:
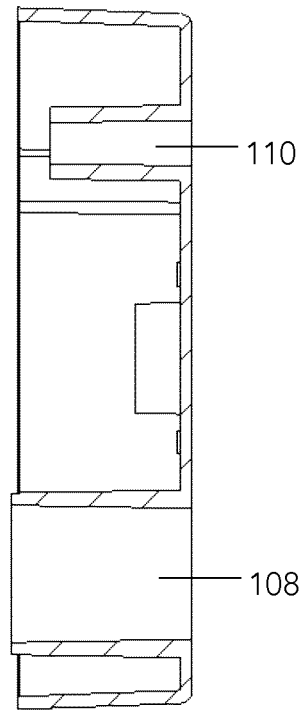
FIG. 2D is a side cross-sectional view of the cover of the concentrating apparatus along line B-B as shown in FIG. 2B.

FIG. 2B is a top view of the cover 102 of a fluid handling apparatus. FIG. 2C is a side cross-sectional view of the cover of the apparatus along line A-A as shown in FIG. 2B showing knob aperture 118. FIG. 2D is a side cross-sectional view of the cover of the apparatus along line B-B as shown in FIG. 2B. Sample aperture 108 and wash aperture 110 extend through the cover to provide supporting apertures where sample and wash syringes, respectively, can be received and aligned with connections in the channel plate to receive fluid.

Figure 3A:
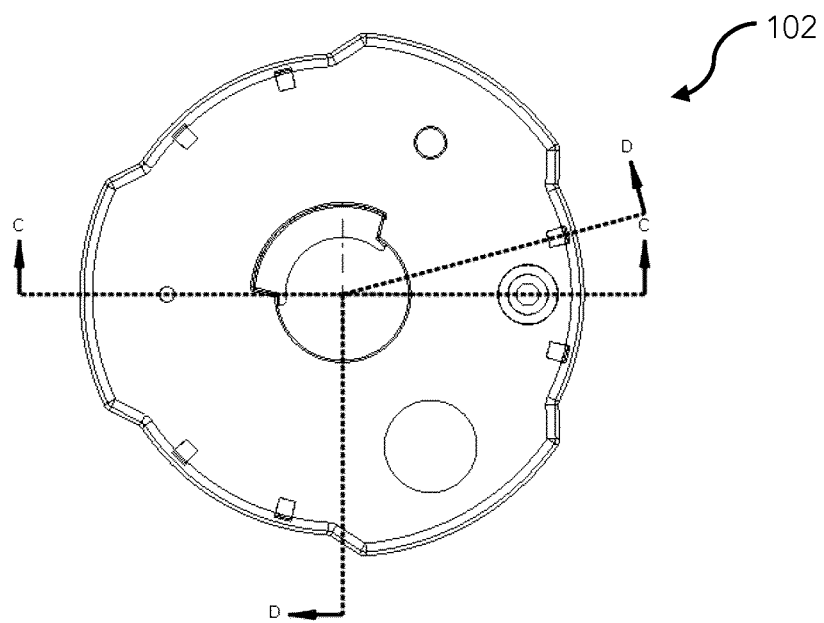
FIG. 3A is a top view of the cover of the concentrating apparatus.
Figure 3B:
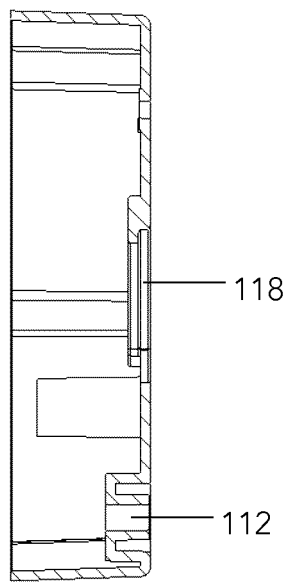
FIG. 3B is a side cross-sectional view of the cover of the concentrating apparatus along line C-C as shown in FIG. 3A.
Figure 3C:
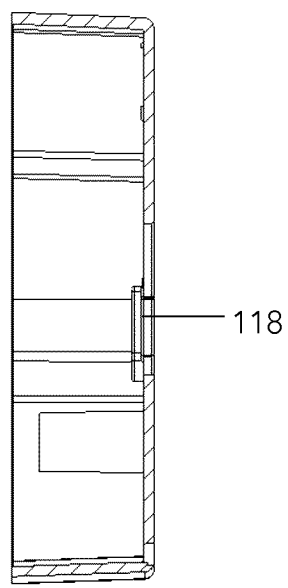
FIG. 3C is a side cross-sectional view of the cover of the concentrating apparatus along line D-D as shown in FIG. 3A.

FIG. 3A is a top view of the cover 102 of a fluid handling apparatus. FIG. 3B is a side cross-sectional view of the cover of the apparatus along line C-C as shown in FIG. 3A showing micro aperture 112 and knob aperture 118. Micro aperture 112 shown is configured to receive the plunger of a microsyringe. The microsyringe plunger dispenses the liquid contained in the apparatus by air displacement. FIG.

3C is a side cross-sectional view of the cover of the apparatus along line D-D as shown in FIG. 3A, with knob aperture 118.

Figure 4A:
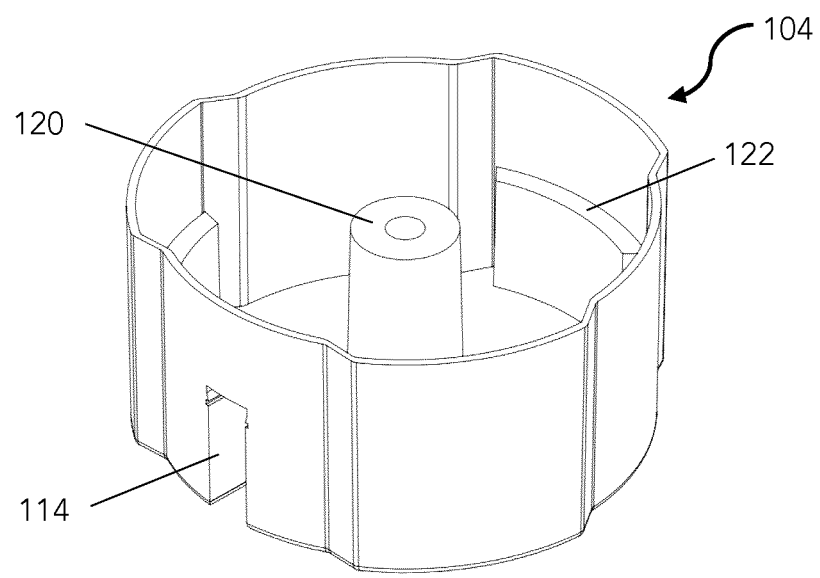
FIG. 4A is a perspective view of the base.
Figure 15:
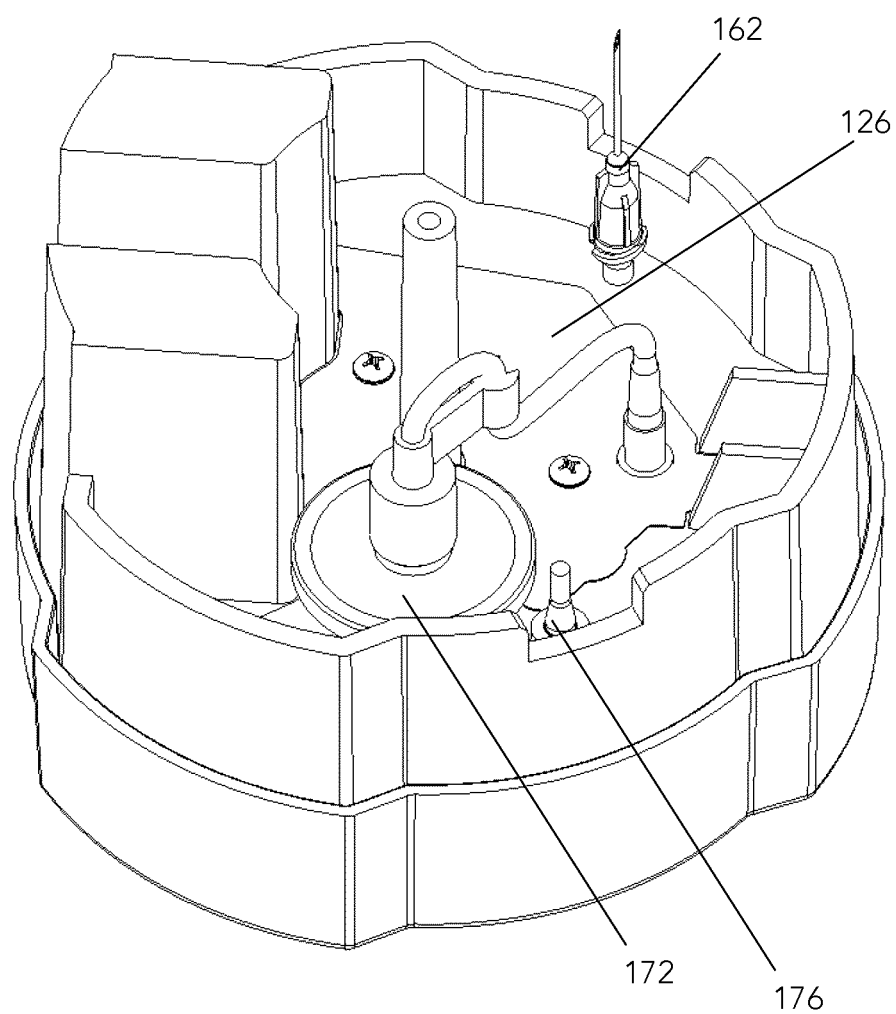
FIG. 15 is bottom perspective view of the midlayer with filter assembly, sealed channel plate, and needle.

FIG. 4A is a perspective view of the base 104 of an apparatus with sample vial port 114. Sample vial port 114 is an aperture to receive and hold a sample vial and/or vial cartridge in alignment with the ejection needle on the channel plate, as shown in FIG. 15. The sample vial port 114 shown has indented guidelines at the top and on either side to secure a sample vial holder such that the sample vial is aligned in the apparatus. Base stem 120 supports a corresponding rod in the midlayer to enable the cover and midlayer to be controllably rotated around the base. Although shown as a matching hollow stem and rod, any structural configuration capable of providing a central rotation axis may be used. Shoulder support 122 provides a horizontal surface to support the midlayer and/or channel plate when it is seated inside the base 104. The stem 120 is to prevent the midlayer 130 from being removed, restricts the height to which the midlayer can be raised, and defines its axis of rotation.

Figure 4B:
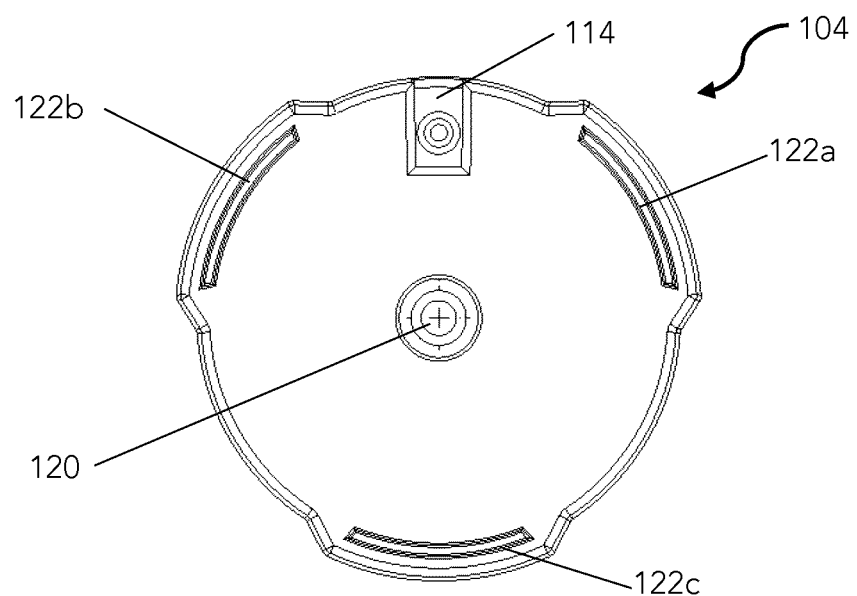
FIG. 4B is a top view of the base.

FIG. 4B is a top view of the base 104 of an apparatus showing shoulder supports 122a, 122b, and 122c and base stem 120. Sample vial port 114 also shows the alignment of a sample vial (concentric circles in the sample vial port 114).

Figure 4C:
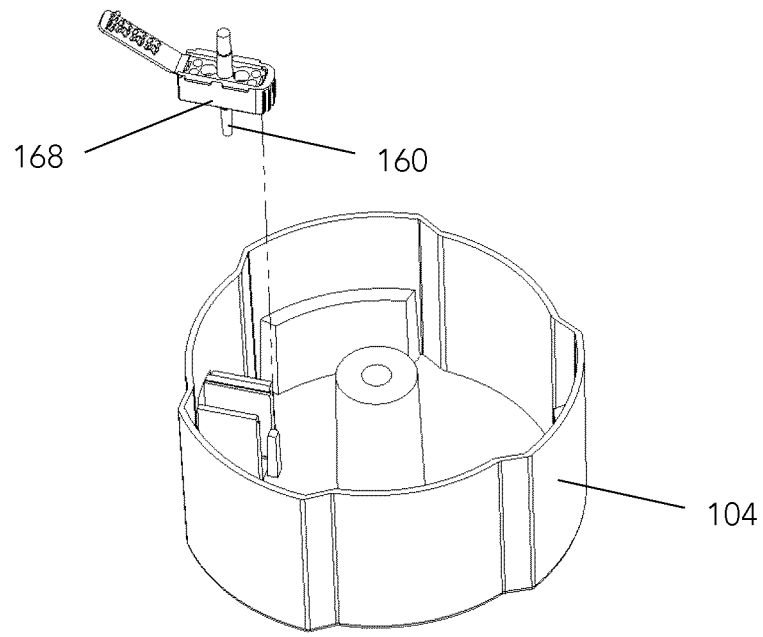
FIG. 4C is an exploded view of the base and vial cartridge.
Figure 4D:
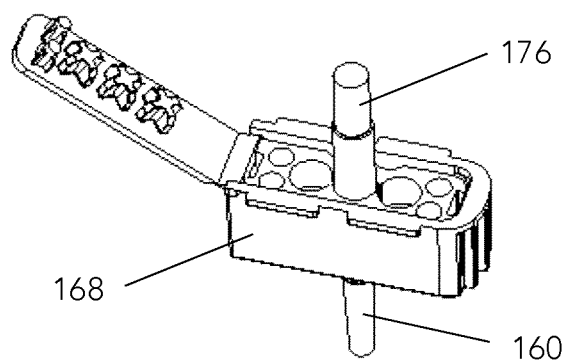
FIG. 4D is a close-up view of a vial cartridge.

FIG. 4C is an exploded view of the base and vial cartridge 168 with sample vial 160. The vial cartridge 168 has a body for holding at least one sample vial 160 and optionally also has a top for sealing the sample vial 160 once concentrated sample has been ejected therein. The sample cartridge 168 shown is adapted to be compatible with PCR amplifiers, such as the Spartan Cube. FIG. 4D is a close-up view of a vial cartridge 168 with sample vial 160. Prior to sample concentration, the sample vial 160 can be plugged with sample vial sealer 176 to seal the vial from potential contamination prior to sample processing. In the midlayer shown in FIG. 6A, a friction seat 178 for the sample vial sealer 176 can be provided to bias the sample vial sealer 176 in place in the sample vial 160 until the apparatus cover and midlayer are lifted and rotated, which removes the sample vial sealer 176 from the sample vial 160 to prepare the sample vial 160 to be filled with concentrated sample. The top of the sample cartridge 168 can also be used as a tab which can be gripped to insert or remove the sample cartridge 168 from the sample vial port 114 once the concentrated sample has been ejected into the sample vial 160, and can also be used to cap the sample cartridge.

Figure 5A:
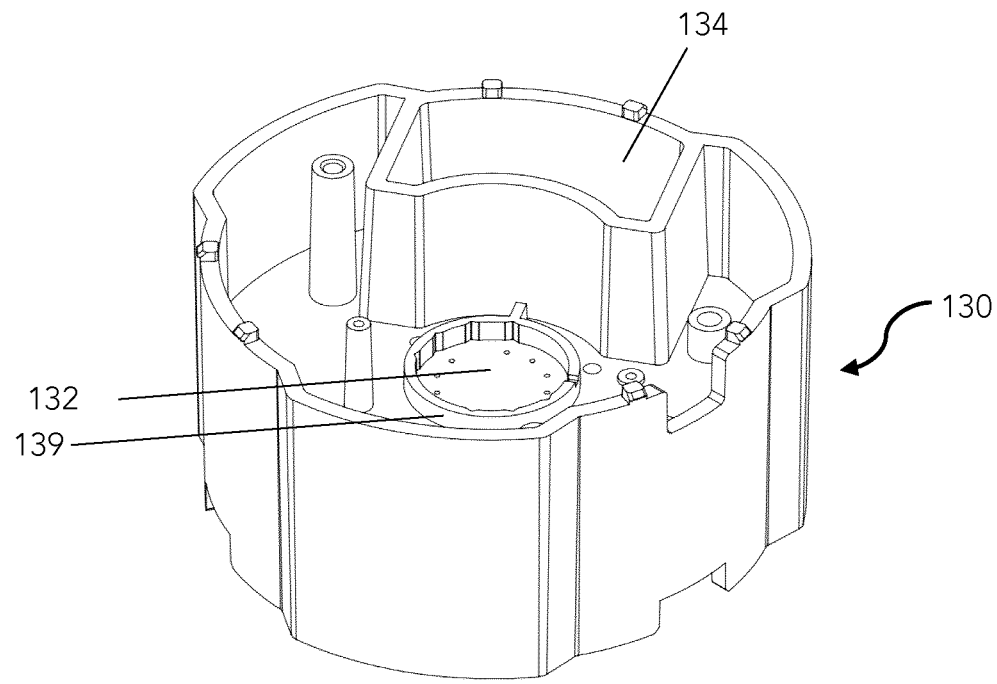
FIG. 5A is a top perspective view of the midlayer.
Figure 5B:
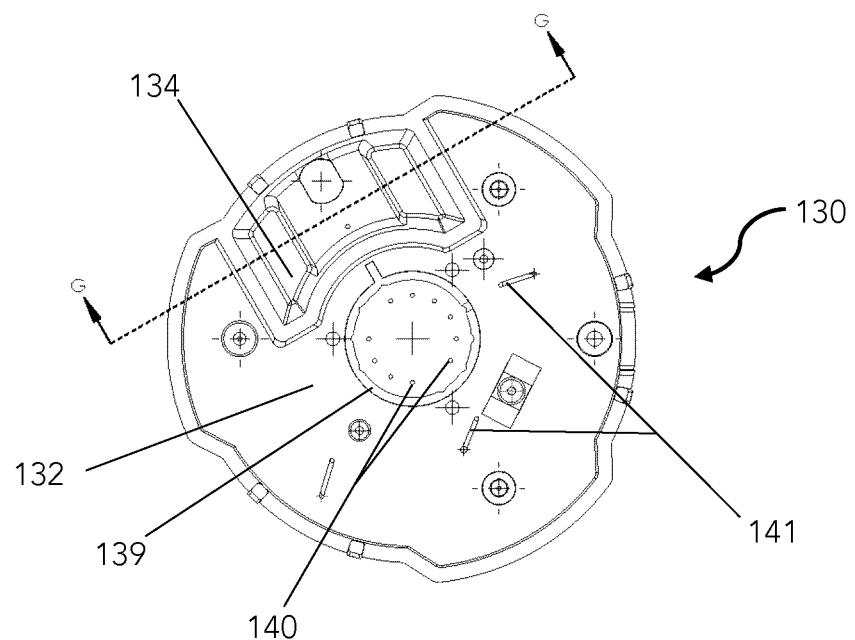
FIG. 5B is a top view of the midlayer with the top of the channel plate.

FIG. 5A is a top perspective view of an apparatus midlayer 130 shown with the top of channel plate 132 and waste reservoir 134. FIG. 5B is a top view of an apparatus midlayer 130 with channel plate 132. Midlayer 130 shown has sidewalls extending perpendicular to the channel plate 132 to support the channel plate 132 and waste reservoir 134. Channel plate 132 comprises a plurality of channel ports 140 which extend through the channel plate, as well as a plurality of fluid channels 141 on the top, bottom, or top and bottom of the channel plate. On the top of the channel plate 132 shown, a plurality of channel ports 140 can be seen disposed in a circular orientation for receiving fluid. The channel ports 140 are connected through the channel plate 132 to fluid channels 141 on the bottom side of the channel plate 132, and are aligned to be fluidly connected by way of the valve channels on a valve plate or rotary valve. Fluid channels 141 on the top of the channel plate 132 provide further fluid paths, including for connecting the input side of the filter to the needle through a channel valve for ejecting concentrated fluid, and for providing an airflow and hydrophobic vent for air venting. A rotary valve housing 139 to support the rotary valve encircles channel ports 140 on the top of the channel plate 132. Rotation guides can also be provided in the rotary valve housing 139 to align the fluid channels on the rotary valve to the channel ports on the channel plate 132. Waste reservoir 134 receives waste fluid after it has been filtered through the filter.

Figure 5C:
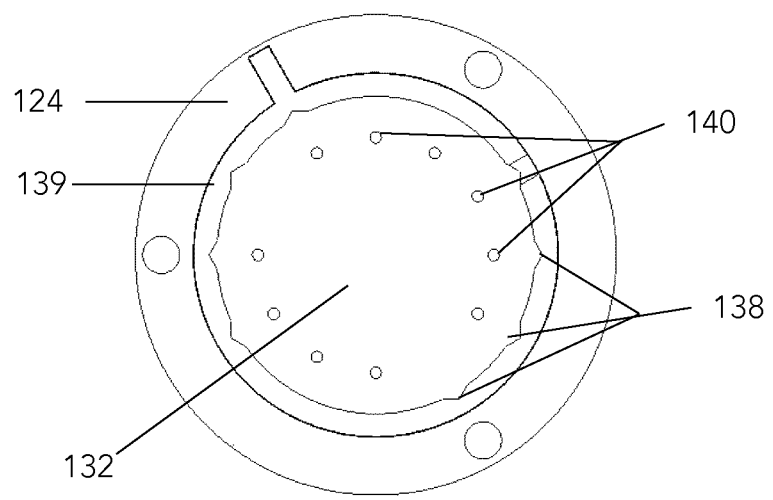
FIG. 5C is a close-up top view of the central part of the channel plate encircled by a valve housing and compression ring.

FIG. 5C is a close-up top view of the central part of the channel plate 132 with a plurality of annularly arranged channel ports 140 configured to align with the channel valves on the rotary valve. There are ten channel ports 140 shown in FIG. 5C, however the number of channel ports can vary depending on the requirements of the apparatus. Compression plate 124 is seated around the rotary valve housing 139 and circle of channel ports 140 in the channel plate 132 to bias the rotary valve against the channel plate 132 and to stabilize the rotation axis of the rotary valve. In the case where the apparatus is not circular and the valve plate does not rotate about a central axis, the compression plate can have any shape which supports compression of a valve plate onto the channel plate. In one alternative example, the compression plate can move about the channel plate in an x-y axis. When the compression plate is a rotary valve, a plurality of rotation guides 138 in the rotary valve housing 139 can extend from the circumference of the rotary valve to align the rotary valve at the desired angle such that the fluid channels on the rotary valve align with the channel ports 140. In the shown configuration the rotation guides 138 are shown as divets in the rotary valve housing 139 with complimentary protrusions in the rotary valve, however the opposite configuration is also possible, as well the number of guides and protrusions can vary based on the number of different channel alignments desired.

Figure 5D:
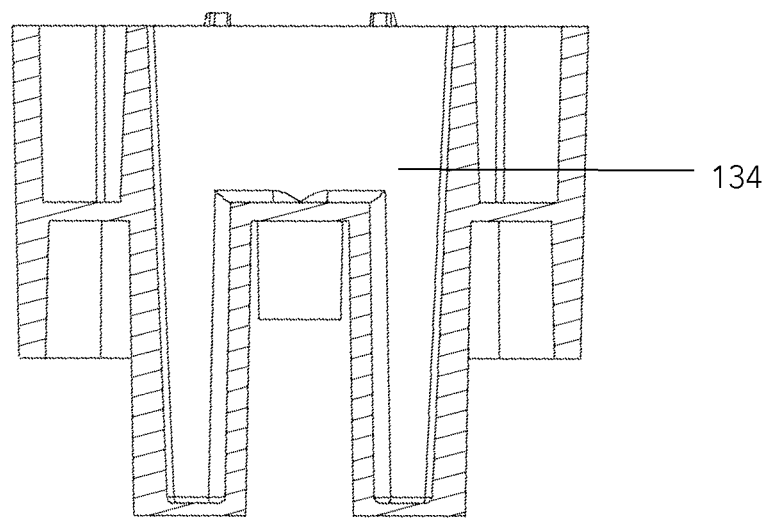
FIG. 5D is a cross-sectional view of the waste reservoir along line G-G as shown in FIG. 5B.

FIG. 5D is a cross-sectional view of waste reservoir 134 along line G-G as shown in FIG. 5B. The volume and shape of waste reservoir 134 can be variable to accommodate a range of waste fluid volumes. In the embodiment shown the waste reservoir extends lower than the body of the midlayer and into the base to accommodate excess filtered waste fluid. The waste reservoir 134 may be empty prior to sample concentration or can optionally also comprise an absorbent material to trap waste fluid and reduce or prevent fluid leak from the apparatus during and/or after use.

Figure 6A:
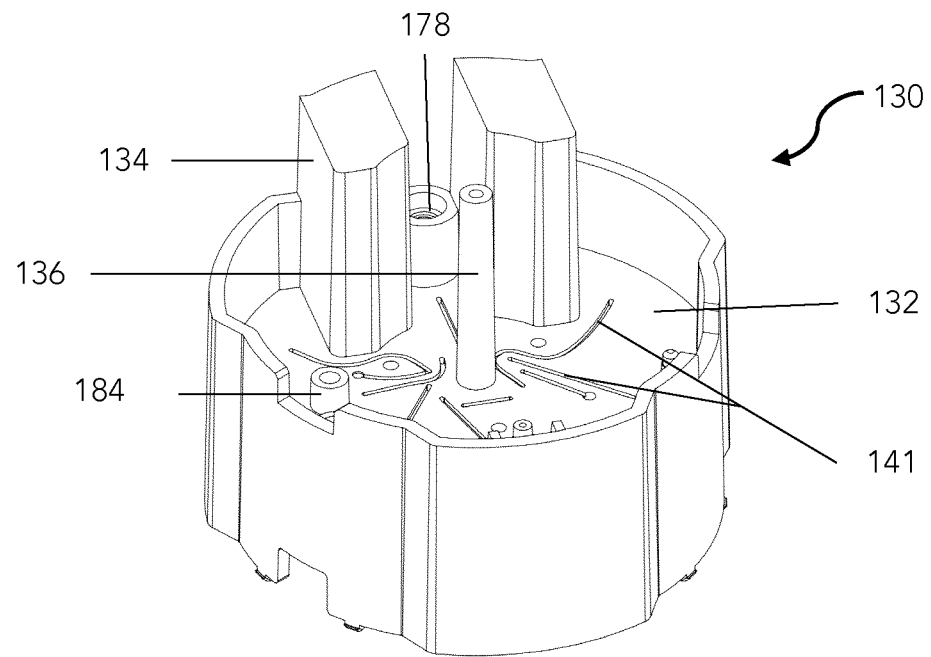
FIG. 6A is a bottom perspective view of the midlayer with a bottom view of the channel plate.
Figure 6B:
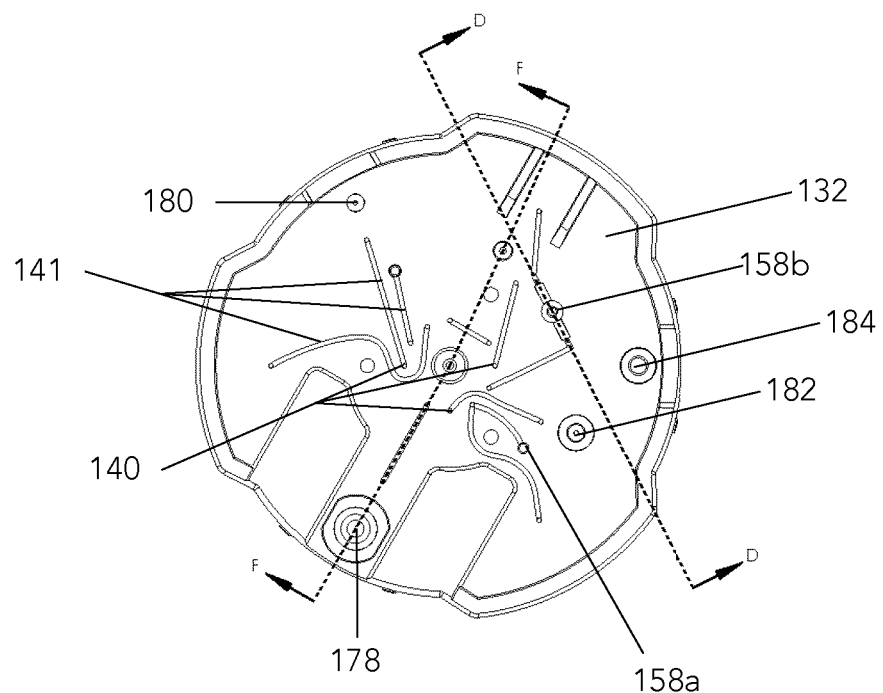
FIG. 6B is a bottom view of the channel plate.

FIG. 6A is a bottom perspective view of the midlayer 130 with a bottom view of the channel plate 132, and FIG. 6B is a bottom view of the channel plate 132. Friction seat 178 for the sample vial plug is shown between the lobes of the waste reservoir 134. Fluid channels 141 on the bottom of the channel plate 132 are connected to channel ports 140 to direct fluid through the channel plate during sample concentrating. Optional hydrophobic vents 158a, 158b provide a mechanism for air to escape from the channels during fluid flow and can seal the channels upon wettening. In one example, a hydrophobic vent (for example, Porex™ part number S001308) can be connected to a syringe to remove the air in the channel preceding the rotary dial (1XX). Midlayer rod 136 extends from the bottom of the midlayer 130 to align with a base stem or other supporting structure to provide an axis of rotation of the midlayer 130 relative to the base. A needle can be connected to the ejection port 180, where concentrated fluid is directed from the filter into the sample vial. The filter is connected to the channel plate 132 through filter port 182. The midlayer 130 can also optionally have a capping rod aperture 184 to receive a capping rod and sample vial cap so that the sample vial can be sealed while the sample vial is still in the apparatus, thus reducing potential contamination during sample handling.

Figure 6C:
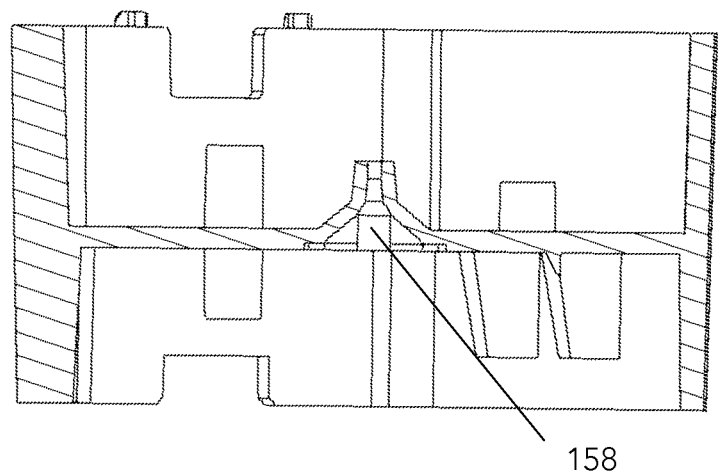
FIG. 6C is a cross-sectional view of the midlayer along line D-D shown in FIG. 6B.

FIG. 6C is a cross-sectional view of the midlayer along line D-D shown in FIG. 6B. Hydrophobic vent 158 is shown as a plug of hydrophobic material inserted into a fluid channel with an aperture open to the air. When the hydrophobic vent is dry, air can escape through the air aperture, however when the hydrophobic material in the hydrophobic vent is wetted the vent becomes fluid tight.

Figure 6D:
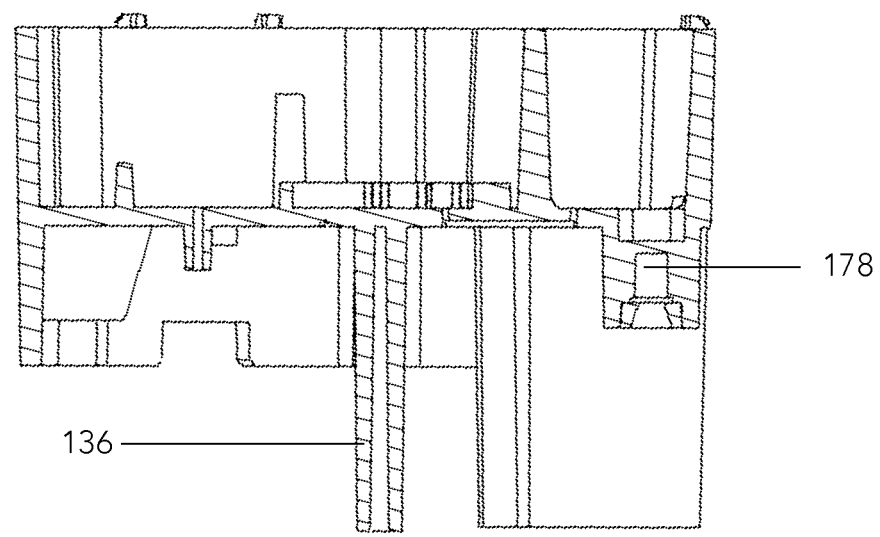
FIG. 6D is a cross-sectional view of the midlayer along line F-F shown in FIG. 6B.

FIG. 6D is a cross-sectional view of the midlayer along line F-F shown in FIG. 6B. The friction seat 178 for the sample vial sealer is shown as a frustoconical aperture with a narrowing to grip the sample vial sealer. The sample vial sealer is preferably made from an elastomeric material so that it can seal against the mouth and/or sides of the sample vial prior to use of the apparatus and be lifted away from the sample vial due to friction grip by the friction seat 178 when the midlayer is rotated about the base around midlayer rod 136.

Figure 7A:
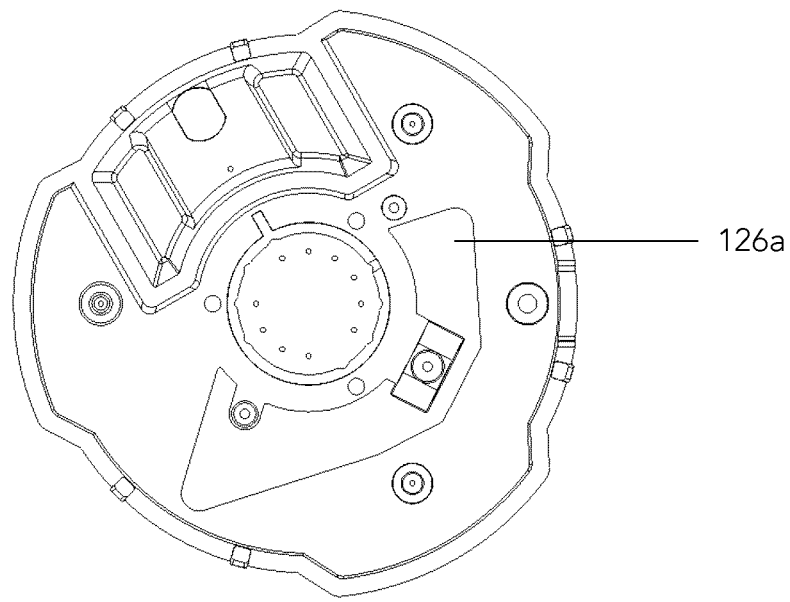
FIG. 7A is a top view of the midlayer with a heat seal covering part of the channel plate.
Figure 7B:
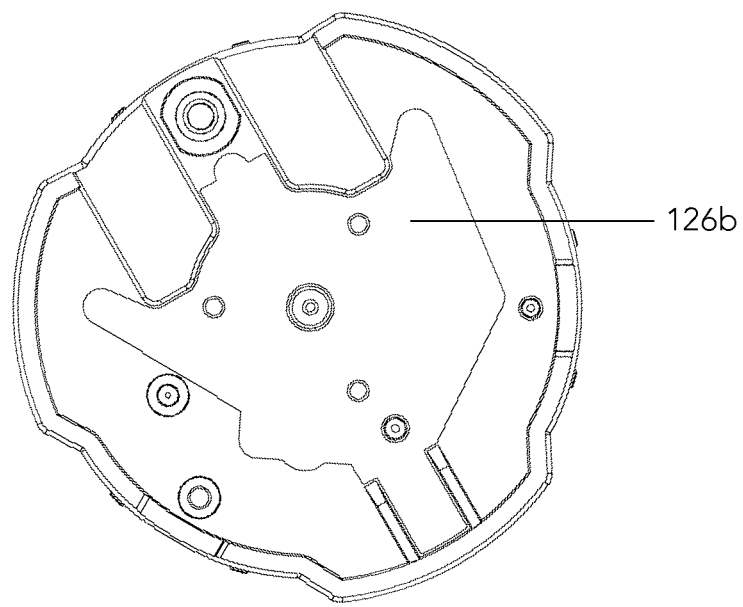
FIG. 7B is a bottom view of the midlayer with a heat seal covering part of the channel plate.

FIG. 7A is a top view of the midlayer with a sealing film 126a covering part of the top of the channel plate. FIG. 7B is a bottom view of the midlayer with a sealing film 126b covering part of the bottom channel plate. The sealing films 126a, 126b seal the fluid channels in the channel plate to provide fluid-tight channels under the pressures applied by the apparatus. The sealing film is preferably heat sealed to the channel plate. In another embodiment, other means can be used to seal the fluid channels in the channel plate, such as, for example, an additional plate with sealing means spatially corresponding to the fluid channels, elastomeric sealing means, or an additional channel plate optionally also comprising fluid channels to further direct fluid from a first channel plate to a second channel plate.

Figure 8A:
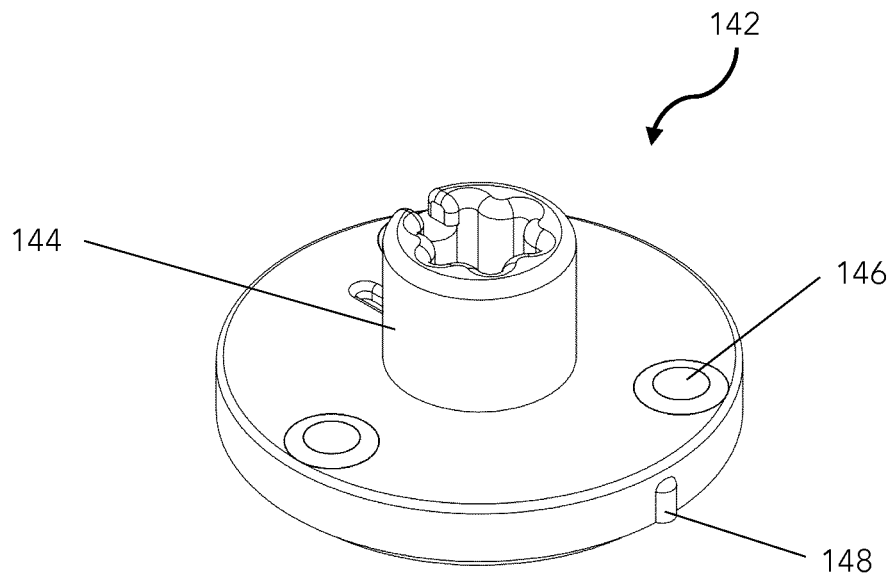
FIG. 8A is a top perspective view of the valve plate.

FIG. 8A is a top perspective view of a rotary valve 142. Rotary valve coupler 144 provides a connection point between the rotary valve and a handle or knob for turning the rotary valve. Compression bump 146 interacts with the compression ring to bias the rotary valve 142 against the channel plate. Alignment pin 148 is a protrusion that extends from the circumference of the rotary valve 142 and aligns with complimentary rotation guides, for example 138a, 138b, on rotary valve housing 139 in FIG. 5C, to align the channel valves on the underside of the rotary valve with the channel ports in the channel plate. Although the alignment pins are shown on the rotary valve with corresponding guides on the channel plate, it is understood that the opposite configuration would also be workable, wherein the rotation guides are on the rotary valve, and the alignment pins are on the channel plate.

Figure 8B:
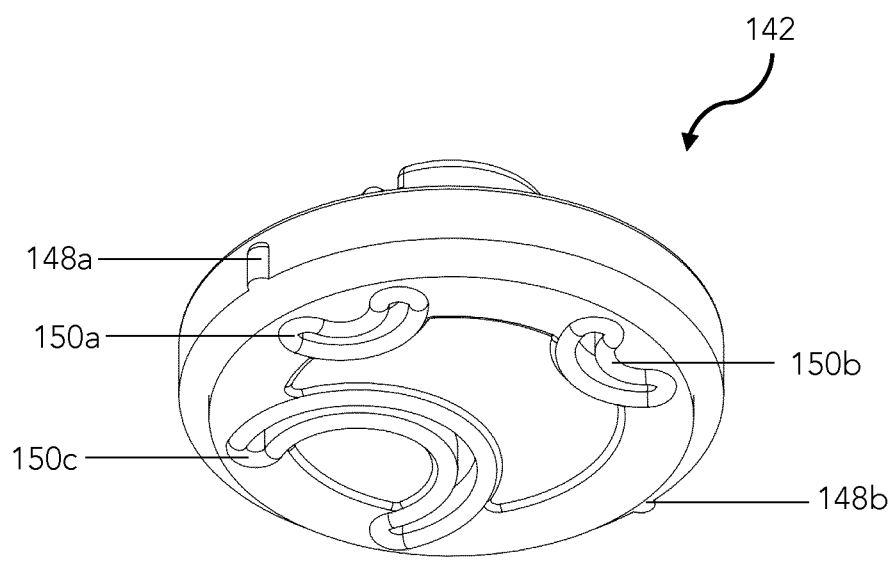
FIG. 8B is a bottom perspective view of the valve plate.

FIG. 8B is a bottom perspective view of rotary valve 142. Rotary valve 142 is shown here with three arced channels valves 150a, 150b, 150c, however it is understood that different configurations of rotary valve and channel plate may allow for fewer or more channel valves, as well as for alternate configuration of the channel valves. Channel valves 150a, 150b, 150c are preferably made of an elastomeric material such that slight pressure applied to the top of the rotary valve 142 will bias the channel valves 150a, 150b, 150c, in a fluid tight and sliding fashion onto the channel plate, creating a fluid tight seal. The relative angular position of the rotary valve can be adjusted about an axis of rotation relative to the channel plate. The channel valves on the rotary valve can thus be angularly aligned with the channel ports on the channel plate, the channel valves being configured to communicate selectively with particular channel ports at different stages in the concentration process. Two alignment pins 148a, 148b are shown extending from the circumference of the rotary valve 142 to align with complimentary rotation guides on the channel plate, although other configurations may have one, or more than two, alignment pins.

Figure 8C:
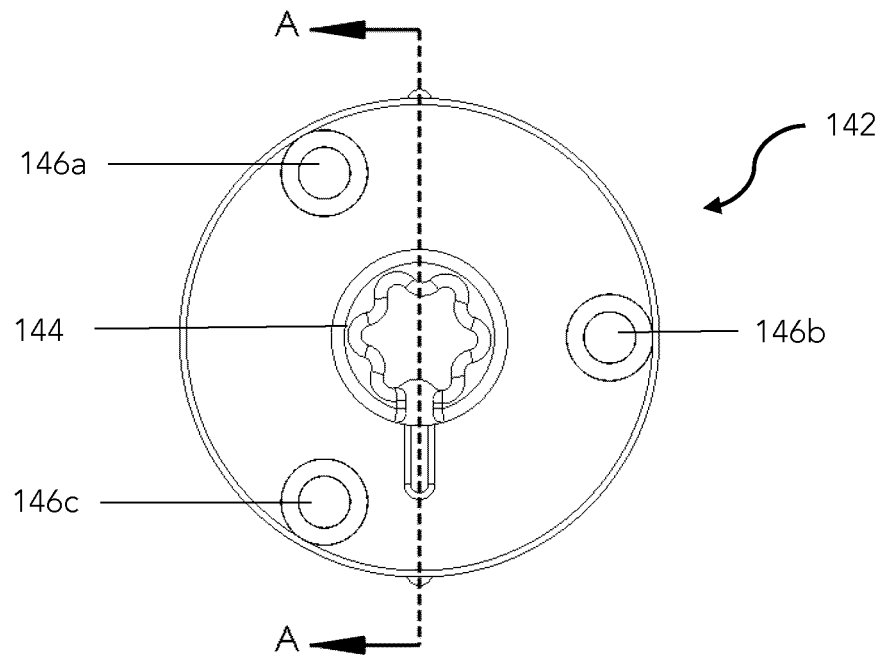
FIG. 8C is a top view of the valve plate.

FIG. 8C is a top view of a rotary valve 142 with rotary valve coupler 144. The top of the rotary valve 142 is shown with compression bumps 146a, 146b and 146c, which are raised features. The compression ring can have complimentary compression divets to receive the compression bumps on the rotary valve in a resting position of the rotary valve such that there is less pressure on the channel valves during transport or when the apparatus is not being used or is in a resting position, preserving the elastomeric properties and thus fluid-tightness of the channel valves. When the rotary valve is rotated away from a resting position (when the compression bumps of the rotary valve are nested inside the compression divets of the compression ring (shown in FIGS. 12A and 12C), the compression ring applies pressure to the channel valves, biasing and sealing the channel valves against the channel plate and creating a substantially fluid-tight seal. Relieving the pressure on the channel valves by aligning the compression bumps of the rotary valve with the compression divets preserves the sealing elastomer and thus the fluidic seal.

Figure 8D:
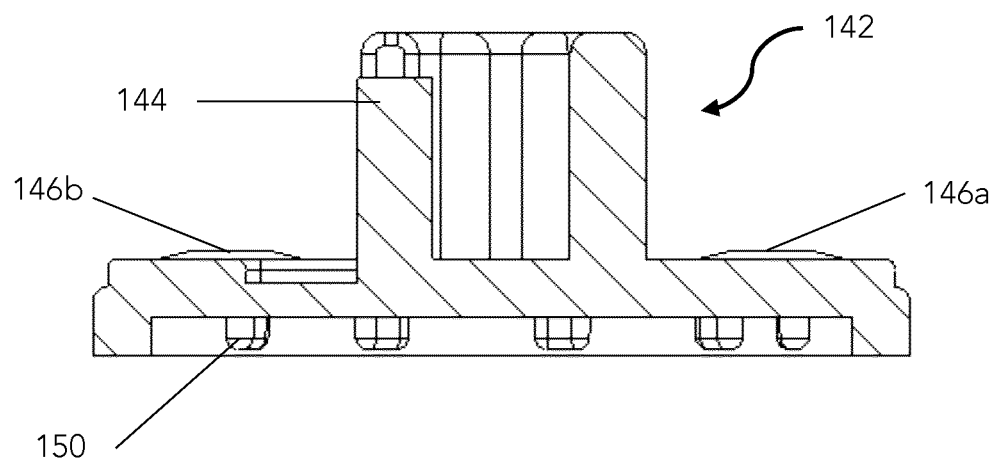
FIG. 8D is a side cross-sectional view of the valve plate.
Figure 8E:
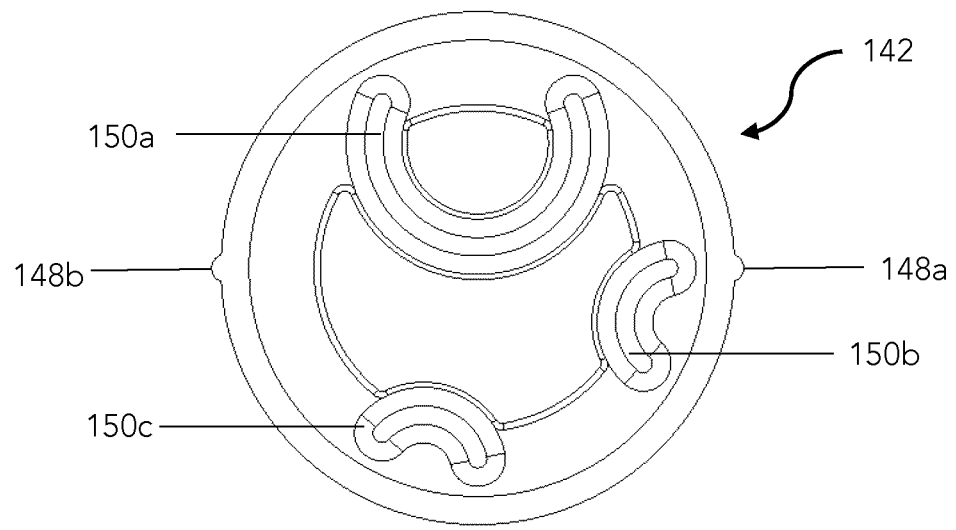
FIG. 8E is a bottom view of the valve plate showing the valve channels.

FIG. 8D is a side cross-sectional view of rotary valve 142 though line A-A in FIG. 8C. The rotary valve 142 has a rotary valve coupler 144 for attaching a knob, and compression bumps 146a, 146b for engaging with and sliding against the compression ring to press channel valve 150 against the channel plate when the apparatus is in use. FIG. 8E is a bottom view of rotary valve 142 showing arced valve channels 150a, 150b and 150c, and alignment pins 148a, 148b.

Figure 8F:
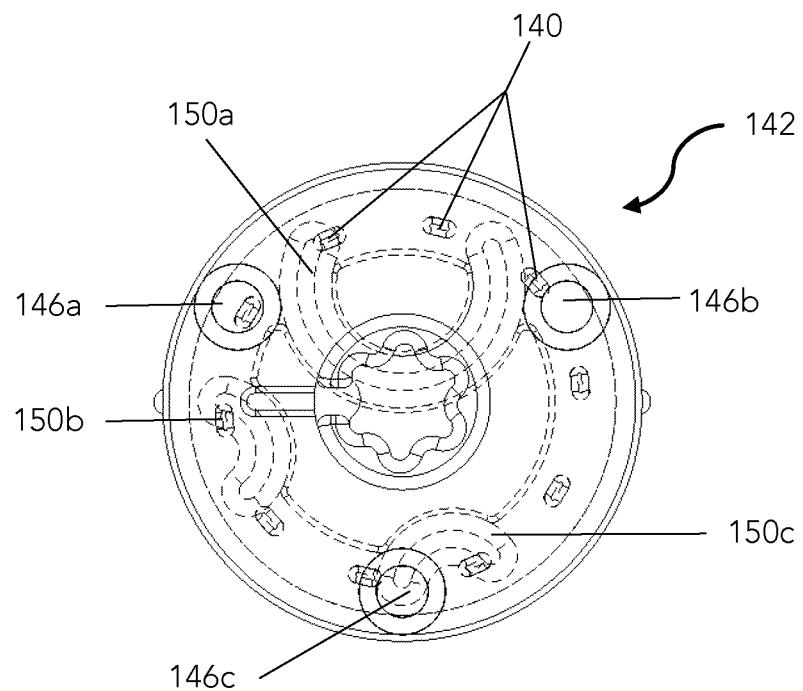
FIG. 8F is a top view of the valve plate showing the valve channels.

FIG. 8F is a transparent top view of the rotary valve 142 shown with arced channel valves 150a, 150b and 150c on the underside and compression bumps 146a, 146b, 146c on top. Also shown is the alignment of valve channels 150a, 150b, and 150c, with annularly arranged channel ports 140 located on the channel plate shown underneath. The rotary valve is rotatable about a central axis between different angular positions so as to permit fluid connection of the channel ports through the channel valves on the rotary valve. The rotary valve acts as an actuating mechanism for moving the channel valves to connect the different channel ports and create fluid passages between channel ports for each step of the concentrating process. Channel valves on the valve plate can be of any shape to fluidly connect at least two fluid channels or channel ports. In other embodiments the channels can be straight, straight with elbows, or differently arced. Channel valves on a valve plate which moves on an x-y axis relative to the channel plate may be more conducive to straighter or diagonal channel valves, while rotational valve plates may be more conducive to arced channel valves. The valve plate may be further adapted to move in both an x-y and rotational plane, and may be further capable of retaining, moving, and/or processing fluid, similar to a secondary channel plate.

Figure 9A:
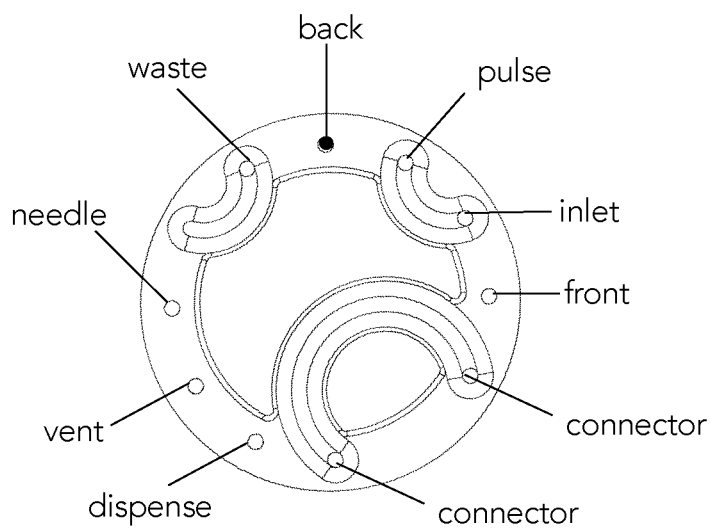
FIGS. 9A-D are schematic views of the bottom of the valve plate with alignment to the fluid channels on the channel plate at a variety of angular displacements around a central axis.
Figure 9B:
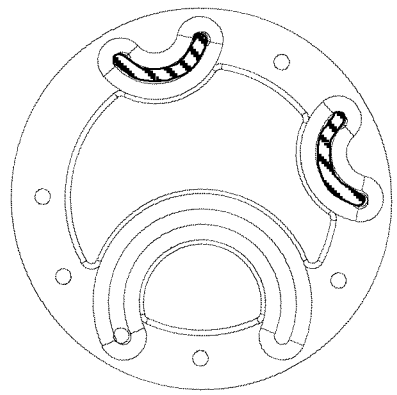
Figure 9C:
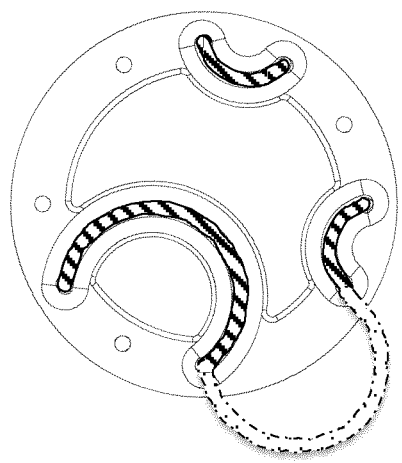
Figure 9D:
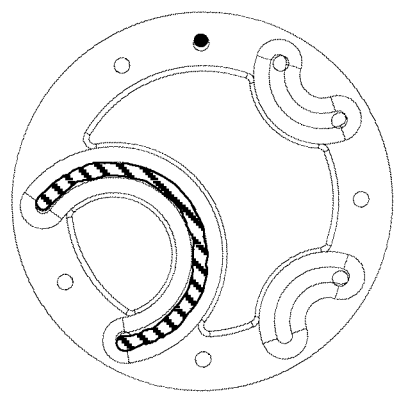

FIGS. 9A-D are schematic views of the bottom of a rotary valve with alignment to the fluid channels on the channel plate at a variety of angular displacements around a central axis. Connection of two of the channel ports on the channel plate to form a fluid path is accomplished by angularly displacing the rotary valve around a central axis relative to the channel plate and connecting two of the channel ports via a channel valve on the rotary valve. As noted in FIGS. 9A-D with the darkened "back" port at the top, the channel ports on the channel plate remain stationary while the rotary valve turns to connect various of the channel ports. In FIG. 9A the rotary valve is shown in a rest position with a view from the top, with the channel valves facing down toward the channel plate. When the rotary valve is turned 30° clockwise from FIG. 9A to FIG. 9B (second position (○) on knob), the dilute sample inlet is connected to the waste reservoir through the channel ports. In particular, inlet port where dilute sample is inserted connects to front port which connects to back port, through front and back channels on the channel plate, which connects to waste port (which connects to the waste reservoir). Once the desired volume of dilute sample is applied to the sample (inlet) port, a second 30° clockwise rotation of the rotary valve to the orientation shown in FIG. 9C to the third (Δ) position connects the back and pulse ports while the front and vent ports are connected through a connector in the channel plate, shown as a dashed channel. A 30° clockwise rotation of the rotary valve to the orientation shown in FIG. 9D to the fourth (□) position connects the dispense port to the needle, allowing the concentrated sample to be ejected through the needle and into the sample vial. A non-rotary or combination rotary/non-rotary valve plate can work in a similar way, with connection of at least one channel valve on the valve plate to the fluid channels and channel ports on the channel plate variable based on the x-y movement of the valve plate against the channel plate.

Figure 10A:
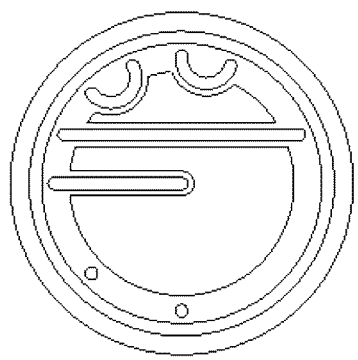
FIG. 10A is a bottom view of a valve plate with an alternative configuration of the channel valves.
Figure 10B:
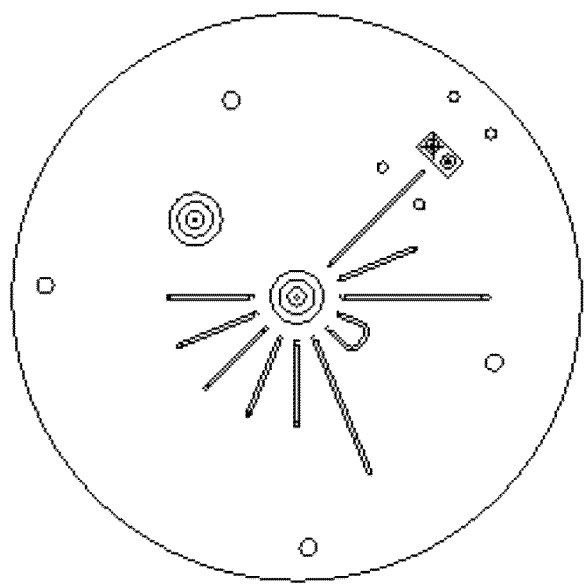
FIG. 10B is an alternative configuration of the channel plate.

FIG. 10A is a bottom view of a rotary valve with an alternative configuration of the channel valves. FIG. 10B is an alternative configuration of the channel plate.

Figure 11A:
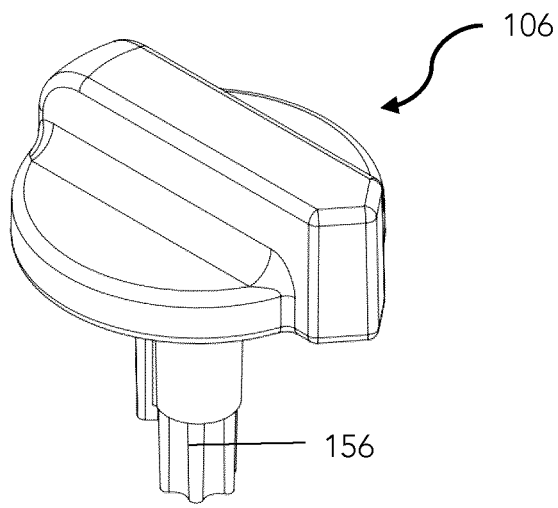
FIG. 11A is a top perspective view of the valve plate knob.
Figure 11B:
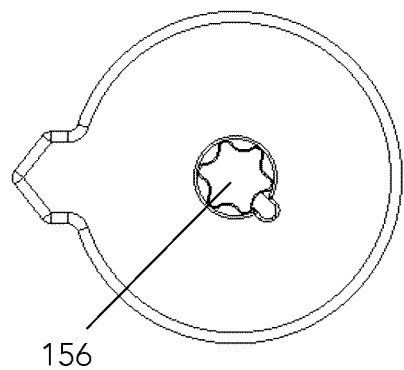
FIG. 11B is a bottom view of the valve plate knob.
Figure 11C:
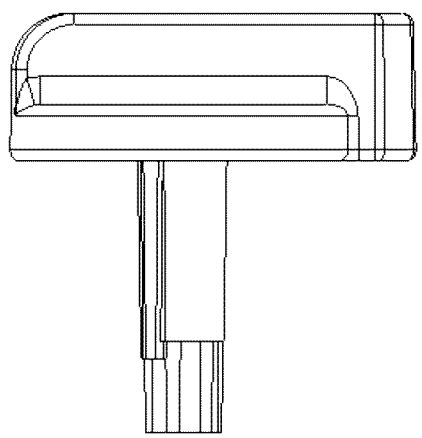
FIG. 11C is a side view of the valve plate knob.
Figure 11D:
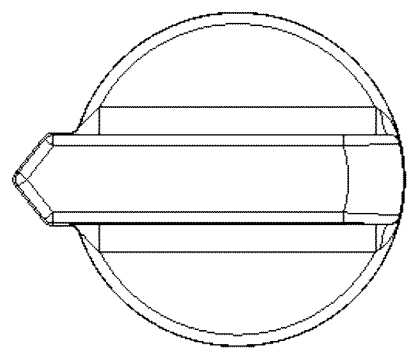
FIG. 11D is a top view of the valve plate knob.

FIG. 11A is a top perspective view of the rotary valve knob 106. Knob stem 156 shown fits into the rotary valve coupler on the rotary valve to allow manual turning of the rotary valve against the channel plate. FIG. 11B is a bottom view of the rotary valve knob showing a star-shaped cross-section of the knob fitting. The end of the knob stem can be any suitable size, shape and configuration capable of engaging with and turning the rotary valve. FIG. 11C is a side view of the rotary valve knob. FIG. 11D is a top view of the rotary valve knob.

Figure 12C:
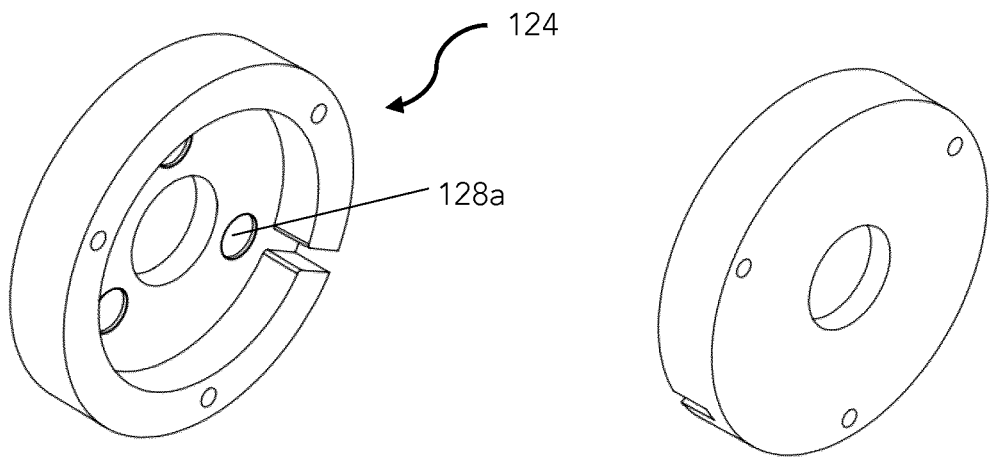
FIG. 12C is a bottom view of the compression ring.
Figure 12C:
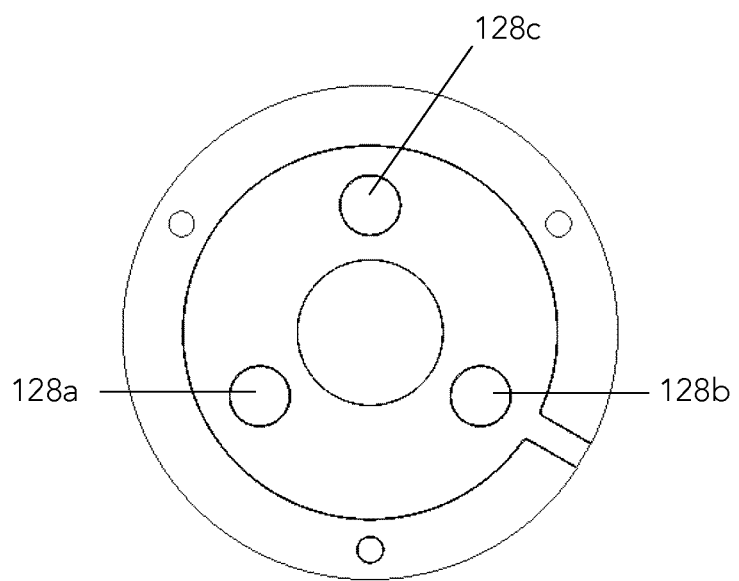

FIGS. 12A-12C are, respectively, a bottom perspective view, top perspective view, and bottom view of the compression plate 124. The compression ring can be used to bias the bottom surface of the rotary valve against the plurality of channel ports to seal the valve channels to the channel plate. In biasing the valve channels of the rotary valve against the channel plate the apparatus is sealed against leak at the pressures applied. Compression divets 128a, 128b, 128c on the inside of the compression ring are configured to receive compression bumps on the top of the rotary valve when the rotary valve is in a rest position. When the rotary valve is engaged, the compression bumps on the top of the rotary valve engage with the flat surface on the inside top of the compression ring and compress the elastomer of the channel valves to the channel plate to form a fluid-tight seal.

Figure 13B:
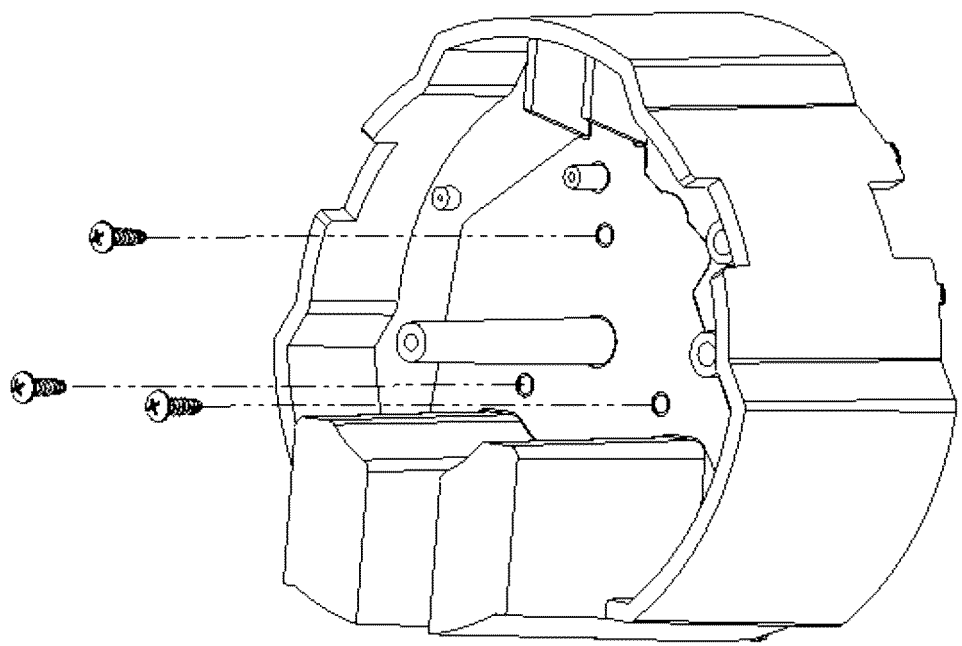
FIG. 13B is an exploded bottom view of the midlayer assembly and sealed channel plate with screws for securing the compression ring.
Figure 13A:
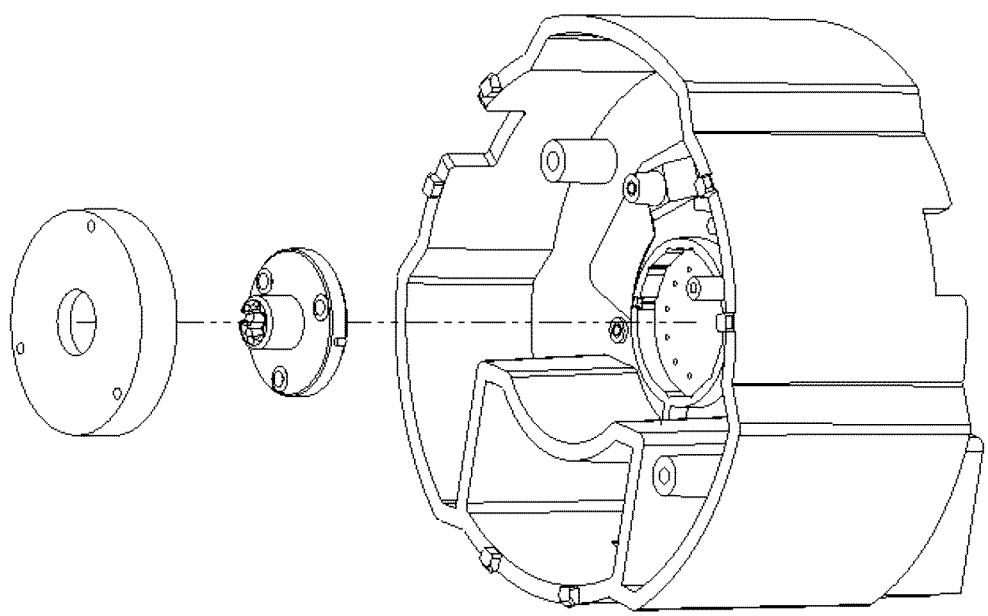
FIG. 13A is an exploded top view of the midlayer assembly and sealed channel plate with valve plate and compression ring.

FIG. 13A is an exploded top view of the midlayer assembly and sealed channel plate showing how the compression ring is assembled around the rotary valve. FIG. 13B is an exploded bottom view of the midlayer assembly and sealed channel plate showing screws for securing the compression ring to the channel plate from the bottom side. Any other attachment means capable of securing the compression ring to the channel plate while still allowing the rotary valve to turn inside the compression ring can also be used.

Figure 14A:
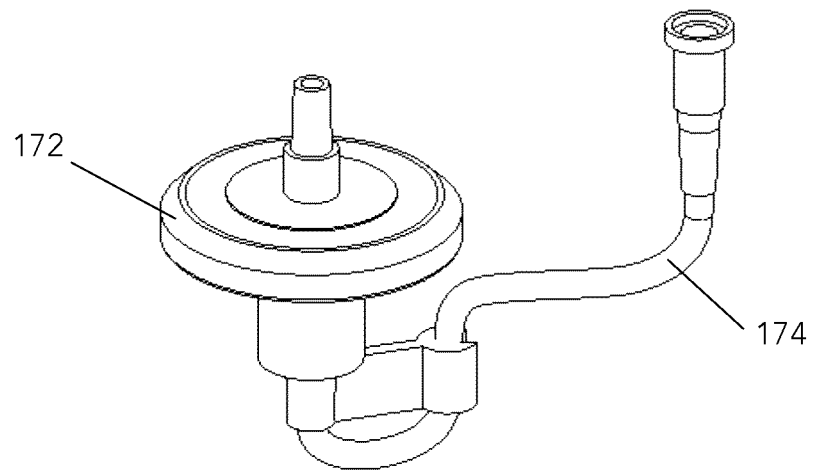
FIG. 14A is a perspective view of a filter assembly with tubing.

FIG. 14A is a perspective view of a filter assembly comprising a filter 172 and tubing 174. Filter 172 has a porous surface for capture of microbiological particles from the fluid sample. Microbiological particles larger than the filter pore size are captured and retained on the surface of the filter, while particles smaller than the pore size of the filter are directed through the filter and flow with the waste fluid into the waste reservoir. Although filter 172 is shown in a vertical orientation it may also be oriented in a horizontal or other orientation. The filter 172 has a membrane having pore sizes from about 0.1 μm to about 100 μm depending on membrane selection. Pore membrane diameter can vary, however the filter pore diameter should provide sterile filtration such that the microbiological particles of interest are retained on the membrane. In one preferable example a 0.45 μm pore diameter membrane can be used for filtration. In another preferable example a 0.22 μm pore diameter membrane can be used. The membrane pore size should be sufficient to retain microbiological particles of interest while allowing fluid to flow through and maintaining reasonable operating pressure in the apparatus. Ranges of membrane pore size can be: 0.1 to 100 μm; 0.1 to 10 μm; and 0.1 to 0.45 μm; 0.1 to 0.22 μm. In a preferable example, the membrane pore diameter is between about 0.2 μm and 0.5 μm. Filter 172 can have a membrane comprised of a variety of materials including but not limited to glass fiber, cellulose ester, mixed cellulose esters, polypropylene, polyacrylonitrile, polyethersulfone, polytetrafluoroethylene, nylon, stainless steel, polycarbonate, polyester, acrylic, polyvinylchloride and ceramics, amongst others.

Figure 14B:
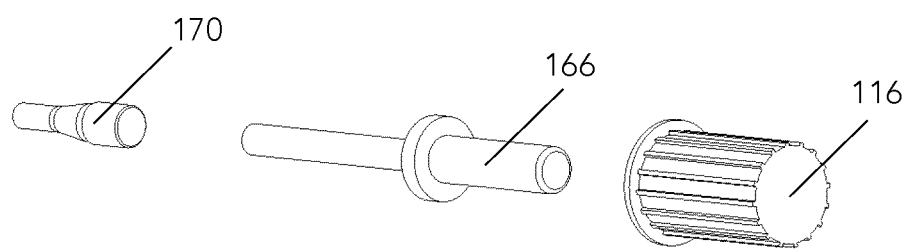
FIG. 14B is a perspective view of a sample vial plug, capping rod, and cap therefor.
Figure 14C:
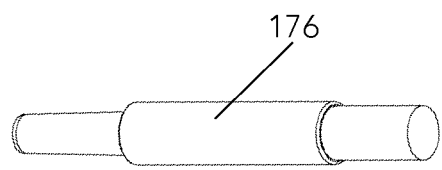
FIG. 14C is a front view of a sample vial sealer.

A capping mechanism can be provided to direct the sample vial cap onto the sample vial while the sample vial is still inside the apparatus. This prevents contamination and enables the capped sample vial to be removed while already sealed. One embodiment of a capping mechanism is a capping rod 166, capping rod cap 116 and sample vial plug 170 shown in FIG. 14B. In the apparatus the capping rod 166 is aligned with the sample vial plug 170 (in capping rod aperture 184 shown in FIG. 6A) such that when the capping rod 166 is depressed, the sample vial plug 170 is released into the sample vial. The capping rod cap 116 (shown also in FIG. 1A) protects the capping rod 166 from inadvertently being depressed until the sample vial is ready to be capped. FIG. 14C is a perspective view of the sample vial sealer 176 which caps the sample vial and prevents contamination before apparatus use.

FIG. 15 is bottom perspective view of the assembled midlayer having filter 172 and needle 162. The channel plate is covered with sealing film 126 and the sample vial sealer 176 is retained in the friction seat.

Figure 16:
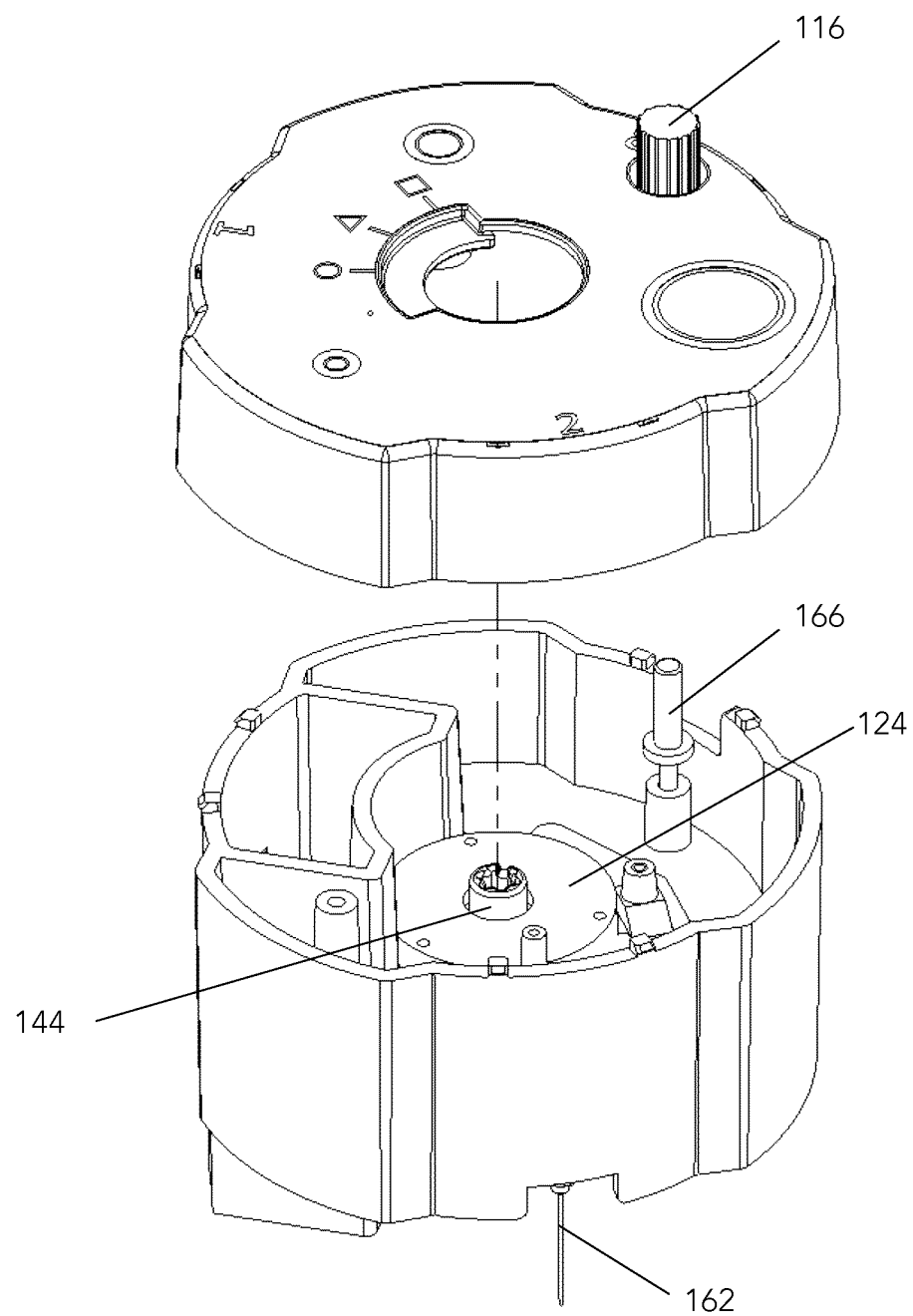
FIG. 16 is a top exploded view of the cover and midlayer.

FIG. 16 is a top exploded view of the assembly of the cover and midlayer. The compression plate 124 is shown attached to the channel plate and securing the rotary valve with the rotary valve coupler 144 extending through the aperture in the compression plate 124 to receive a knob stem. Capping rod cap 116 protects the capping rod 166 from inadvertently being depressed until the sample vial is ready to be capped. Needle 162 aligns with the sample vial to eject concentrated sample into the sample vial after concentrating.

Figure 17A:
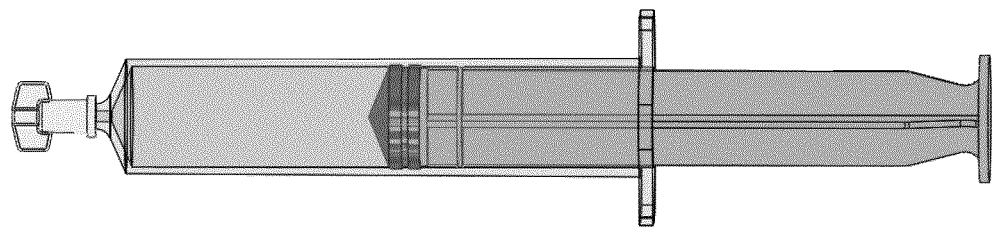
FIG. 17A is a side view of a sample syringe with cap on and off.
Figure 17A:
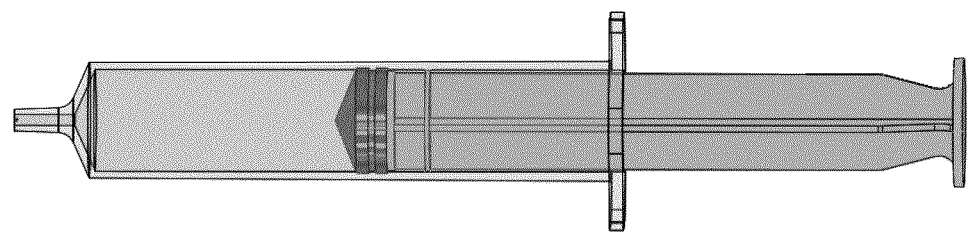
Figure 17B:
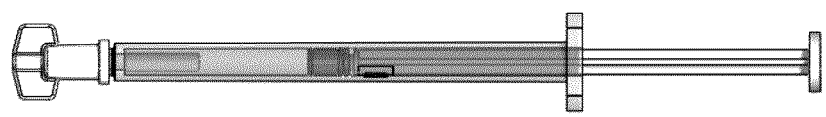
FIG. 17B is a side view of a wash syringe with cap on and off.
Figure 17B:
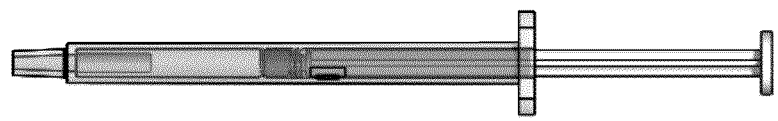
Figure 17C:
FIG. 17C is a side view of a micro syringe barrel.

FIG. 17A shows two side views of a sample syringe with cap on (top) and off (bottom). The sample syringe can be used to aspirate sample fluid to be tested and inject the sample fluid on the apparatus. FIG. 17B shows two side views of a wash syringe with cap on (top) and off (bottom). The wash syringe can be provided pre-filled with wash fluid to wash off potential contaminants and inhibitors from the analyte on the filter. Non-limiting examples of wash fluid can include water or buffer. A contaminant could be any material that interferes with later analysis or stability of the collected concentrated sample. FIG. 17C is a side view of a micro syringe barrel. A kit can be provided with the sample concentrating apparatus as claimed with a combination of one of each of these syringes.

Figure 18:
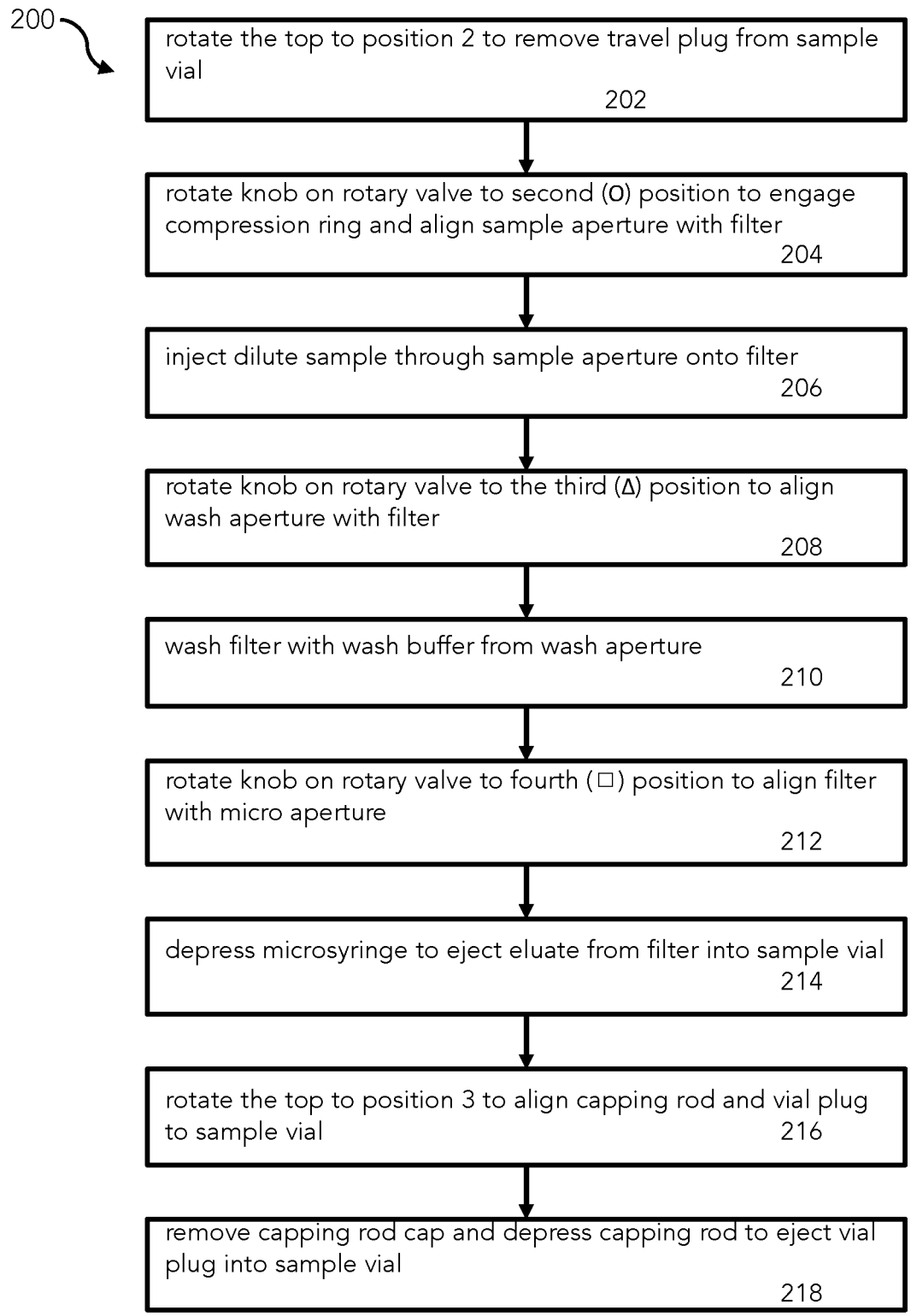
FIG. 18 is a flowchart illustrating a method of concentrating a sample with a valve plate concentrating apparatus.

FIG. 18 is a flowchart illustrating a method of concentrating a sample with a rotary fluid handling apparatus as described. It is understood that a similar method can be used with a non-rotary apparatus by instead moving the valve plate in an x-y direction relative to the channel plate, and moving the channel plate relative to the housing at an appropriate rotation for the apparatus. The apparatus can be provided in a kit with a sample syringe, wash syringe, and a microsyringe barrel. The apparatus is provided with position 1 (see FIG. 1A) aligned with the sample vial port. To prepare the apparatus for infusion of dilute sample, the top of the apparatus is slightly lifted relative to the base, and the top is rotated clockwise so that position 2 is aligned with the sample vial port 202. This rotation of the top relative to the base removes a sample vial sealer, which is retained by friction by the midlayer, from the sample vial. The friction seat for the sample vial sealer is shown as feature 178 in FIG. 6A and the sample vial sealer is shown in FIG. 14C.

To prepare the apparatus for receiving dilute liquid sample, the knob and rotary valve is rotated from the storage position (•) to the second (○) position to engage compression ring and align sample port with filter 204, as shown in FIG. 1A. Dilute sample is collected and aspirated into the sample syringe. The dilute sample is then injected through the sample aperture in the top of the apparatus onto filter 206 and the fluid flowing through the filter is directed to the waste reservoir. Microbiological particles of a size larger than the filter pore size are retained on the filter. The knob on the rotary valve is then rotated to a third (Δ) position to align wash aperture with filter 208. The filter is then washed with wash buffer from wash aperture 210. The knob on the rotary valve is then rotated to the fourth (□) position to align the filter with micro aperture 212.

The microsyringe is then put into the micro port to eject eluate from the filter into the sample vial 214. It has been found that pumping the syringe barrel of the elution syringe (FIG. 17B) at least twice to a predetermined distance assists in eluting the microbiological sample off of the filter A pulsing action in which elution fluid is pulsed retains microbiological particles near the filter while assisting with release of particles from the filter. It has further been found that 10 pulses provides adequate releasing of microbiological particles from the filter. More pulses may enable recovery of more microbiological particles. Pumping at least 5 times, at least 8 times and preferably at least 10 times can assist in releasing the microbiological particles of interest from the filter. The concentrated fluid is then drawn into the channel plate. The concentrated sample is then ejected into the sample vial through the needle by depressing the microsyringe in the micro port 214.

Once the top is rotated to position 3 the capping rod and vial plug are aligned with the sample vial 216. The capping rod cap is then removed and the capping rod is depressed to eject the vial plug into sample vial 218. Collected concentrated can be analyzed for presence and concentration of microbiological particles, such as, for example, via a nucleic acid amplification reaction. Further processing of the concentrated sample can assist in identifying as well as quantifying the amount of microorganism in the dilute fluid sample. Some non-limiting examples of processing can include polymerase chain reaction (PCR), real time PCR, reverse transcription realtime PCR, culturing or incubation, plating and enumeration, antigen detection, immunoassay, electrochemical, microarray, flow cytometry, biosensors, lab-on-a-chip, and rapid growth based detection technologies, to name a few. In a preferable example, the concentrated sample is collected with a micro syringe and PCR analysis is done at the site of sample collection using a mobile PCR unit.

Additional wash or manipulation steps can also be done prior to dispensing the concentrated sample, non-limiting examples include wash steps, labeling steps, cell lysis, or other manipulation.

It should be understood that arrangements and components described herein are for the purposes of example only. As such, those skilled in the art will appreciate that other arrangements, configurations, structures, and elements can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

All publications, patents and patent applications mentioned in this specification are indicative of the level of skill of those skilled in the art to which this invention pertains and are herein incorporated by reference. The invention being thus described, it will be obvious that the same may be varied in many ways. Such variations are not to be regarded as a departure from the scope of the invention, and all such modifications as would be obvious to one skilled in the art are intended to be included within the scope of the following claims.

We claim:

1. A fluid handling apparatus comprising:
   a channel plate having a first face and a second face, the channel plate comprising:
     a plurality of channel ports extending from the first face to the second face for directing fluid between the first face and the second face of the channel plate;
     a plurality of fluid channels, the fluid channels on the first face and the second face of the channel plate, each fluid channel fluidly connected to at least one channel port, wherein each of the fluid channels connects to a channel port of the plurality of channel ports extending from the first face to the second face;
     a sample port for receiving fluid to be handled, the sample port fluidly connected to at least one of the plurality of fluid channels; and
     an exit port for extracting fluid from the fluid handling apparatus,
     wherein the first face and the second face of the channel plate are sealed to fluidly encase the fluid channels; and
   a valve plate movable relative to the channel plate, the valve plate comprising at least one channel valve to fluidly connect at least two of the plurality of channel ports and fluid channels, wherein the valve plate is a rotary valve comprising:
     a top surface comprising a knob to control rotation of the rotary valve about a central axis; and
     a bottom surface comprising the at least one channel valve; and
     wherein the channel plate comprises an annular housing to support the rotary valve, and the rotary valve and housing comprises complimentary alignment pins and rotation guides to angularly align the rotary valve relative to the plurality of channel ports.

2. The apparatus of claim 1, wherein the first face and the second face of the channel plate are sealed with a sealing film.

3. The apparatus of claim 1, wherein the channel plate has a top side and a bottom side, and wherein the channel plate comprises fluid channels on both the top side and the bottom side.

4. The apparatus of claim 1, further comprising a hydrophobic vent in at least one of the plurality of fluid channels.

5. The apparatus of claim 1, wherein the plurality of channel ports are arranged annularly around an axis.

6. The apparatus of claim 1, wherein the channel plate is fluidly connected to a waste reservoir.

7. The apparatus of claim 1, wherein the channel plate further comprises a wash aperture.

8. The apparatus of claim 1, further comprising a base.

9. The apparatus of claim 1, further comprising a filter fluidly connected to at least one of the plurality of fluid channels.

10. The apparatus of claim 1, wherein the valve plate is compressible against the channel plate.

11. The apparatus of claim 10, wherein the valve plate comprises at least one of elastomer and an elastomer gasket.

12. The apparatus of claim 1, further comprising a compression plate to compress the channel valve of the valve plate against the channel plate.

13. The apparatus of claim 1, wherein the valve plate comprises a plurality of channel valves.

14. The apparatus of claim 12, wherein the compression plate and rotary valve comprise complimentary divets and compression bumps to bias the rotary valve against the channel plate.

15. The apparatus of claim 8, further comprising a cover.

16. The apparatus of claim 15, wherein the cover is movable relative to the base.

17. The apparatus of claim 15, wherein the cover is rotatable relative to the base.

18. The apparatus of claim 1, wherein the channel plate is supported by a sidewall.

19. A fluid handling apparatus comprising:
a channel plate having a first face and a second face, the channel plate comprising :
a plurality of channel ports extending from the first face to the second face for directing fluid between the first face and the second face of the channel plate; a plurality of fluid channels, the fluid channels on the first face and the second face of the channel plate, each fluid channel fluidly connected to at least one channel port, wherein each of the fluid channels connects the channel ports extending from the first face to the second face;
a sample port for receiving fluid to be handled, the sample port fluidly connected to at least one of the plurality of fluid channels; and
an exit port for extracting fluid from the fluid handling apparatus, wherein the first face and the second face of the channel plate are sealed to fluidly encase the fluid channels;
a valve plate movable relative to the channel plate, the valve plate comprising at least one channel valve to fluidly connect at least two of the plurality of channel ports and fluid channels, wherein the valve plate is a rotary valve comprising:
a top surface comprising a knob to control rotation of the rotary valve about a central axis; and
a bottom surface comprising the at least one channel valve; and
a compression plate to compress the channel valve of the valve plate against the channel plate wherein the compression plate and rotary valve comprise complimentary divets and compression bumps to bias the rotary valve against the channel plate.

20. The apparatus of claim 19, wherein the first face and the second face of the channel plate are sealed with a sealing film.

21. The apparatus of claim 19, wherein the channel plate has a top side and a bottom side, and wherein the channel plate comprises fluid channels on both the top side and the bottom side.

22. The apparatus of claim 19, further comprising a hydrophobic vent in at least one of the plurality of fluid channels.

23. The apparatus of claim 19, wherein the plurality of channel ports are arranged annularly around an axis.

24. The apparatus of claim 19, wherein the channel plate is fluidly connected to a waste reservoir.

25. The apparatus of claim 19, wherein the channel plate further comprises a wash aperture.

26. The apparatus of claim 19, further comprising a base.

27. The apparatus of claim 19, further comprising a filter fluidly connected to at least one of the plurality of fluid channels.

28. The apparatus of claim 19, wherein the valve plate is compressible against the channel plate.

29. The apparatus of claim 28, wherein the valve plate comprises at least one of elastomer and an elastomer gasket.

30. The apparatus of claim 19, wherein the valve plate comprises a plurality of channel valves.

31. The apparatus of claim 26, further comprising a cover.

32. The apparatus of claim 31, wherein the cover is movable relative to the base.

33. The apparatus of claim 31, wherein the cover is rotatable relative to the base.

34. The apparatus of claim 19, wherein the channel plate is supported by a sidewall.

* * * * *